US010266584B2

(12) United States Patent
Reynard et al.

(10) Patent No.: US 10,266,584 B2
(45) Date of Patent: Apr. 23, 2019

(54) ANTIBODIES SPECIFIC TO GLYCOPROTEIN (GP) OF *EBOLAVIRUS* AND USES FOR THE TREATMENT AND DIAGNOSIS OF EBOLA VIRUS INFECTION

(71) Applicants: INSERM (INSTITUT NATIONAL DE LA SANTÉ ET DE LA RECHERCHE MÉDICALE), Paris (FR); UNIVERSITÉ CLAUDE BERNARD—LYON 1, Villeurbanne (FR); ENS—ECOLE NORMALE SUPÉRIEURE DE LYON, Lyons (FR); CENTRE NATIONAL DE LA RECHERCHE SCIENTIFIQUE (CNRS), Paris (FR)

(72) Inventors: Olivier Reynard, Lyons (FR); Viktor Volchkov, Lyons (FR)

(73) Assignees: INSERM (Institut National de la Sante et de la Recherche Medicale), Paris (FR); Université Claude Bernard—Lyon 1, Villeurbanne (FR); ENS—Ecole Normale Superieure de Lyon, Lyons (FR); Centre National de la Recherche Scientifique (CNRS), Paris (FR)

(*) Notice: Subject to any disclaimer, the term of this patent is extended or adjusted under 35 U.S.C. 154(b) by 0 days.

(21) Appl. No.: 15/548,883

(22) PCT Filed: Feb. 8, 2016

(86) PCT No.: PCT/EP2016/052614
§ 371 (c)(1),
(2) Date: Aug. 4, 2017

(87) PCT Pub. No.: WO2016/128349
PCT Pub. Date: Aug. 18, 2016

(65) Prior Publication Data
US 2018/0016322 A1    Jan. 18, 2018

Related U.S. Application Data

(60) Provisional application No. 62/113,597, filed on Feb. 9, 2015.

(30) Foreign Application Priority Data

Feb. 10, 2015  (EP) ..................................... 15305191
Mar. 6, 2015   (EP) ..................................... 15305348

(51) Int. Cl.
*C07K 16/10*    (2006.01)
*G01N 33/569*   (2006.01)

(52) U.S. Cl.
CPC ....... *C07K 16/10* (2013.01); *G01N 33/56983* (2013.01); *C07K 2317/33* (2013.01); *C07K 2317/34* (2013.01); *C07K 2317/565* (2013.01); *C07K 2317/76* (2013.01); *G01N 2333/08* (2013.01)

(58) Field of Classification Search
None
See application file for complete search history.

(56) References Cited

FOREIGN PATENT DOCUMENTS

WO    2009/094755 A1    8/2009
WO    2011/071574 A2    6/2011

OTHER PUBLICATIONS

Lee et al. "Structure of the Ebola virus glycoprotein bound to an antibody from a human survivor", Nature, 2008, 454:177-183.*
Coleman P. M. (Research in Immunology, 145:33-36, 1994.*
Paul, Fundamental Immunology, 3 rd Edition, 1993, pp. 292-295.*
Rudikoff et al (Proc. Natl. Acad. Sci. USA, 79:1979-1983, Mar. 1982.*
Lee et al., "Structure of the Ebola virus glycoprotein bound to an antibody from a human survivor", Nature, Jul. 10, 2008, pp. 177-182, vol. 454, No. 7201.
Reynard et al., "Ebolavirus Glycoprotein GP Masks both Its Own Epitopes and the Presence of Cellular Surface Proteins", Journal of Virology, Sep. 15, 2009, pp. 9596-9601, vol. 83, No. 18.
Schornberg et al., "Role of Endosomal Cathepsins in Entry Mediated by the Ebola Virus Glycoprotein", Journal of Virology, Apr. 15, 2006, pp. 4174-4178, vol. 80, No. 8.
Maruyama et al., "Recombinant Human Monoclonal Antibodies to Ebola Virus", Journal of Infectious Diseases, Feb. 1, 1999, pp. S235-S239, vol. 179, No. Suppl. 01, University of Chicago Press, Chicago, IL.

* cited by examiner

*Primary Examiner* — Shanon A. Foley
*Assistant Examiner* — Myron G Hill
(74) *Attorney, Agent, or Firm* — W & C IP

(57) ABSTRACT

The present invention relates to antibodies or fragments thereof that specifically bind to glycoprotein (GP) of Ebola virus, and to their use for treating and diagnosing Ebola virus disease.

9 Claims, 6 Drawing Sheets
Specification includes a Sequence Listing.

Figure 1 A and B

Figure 1:
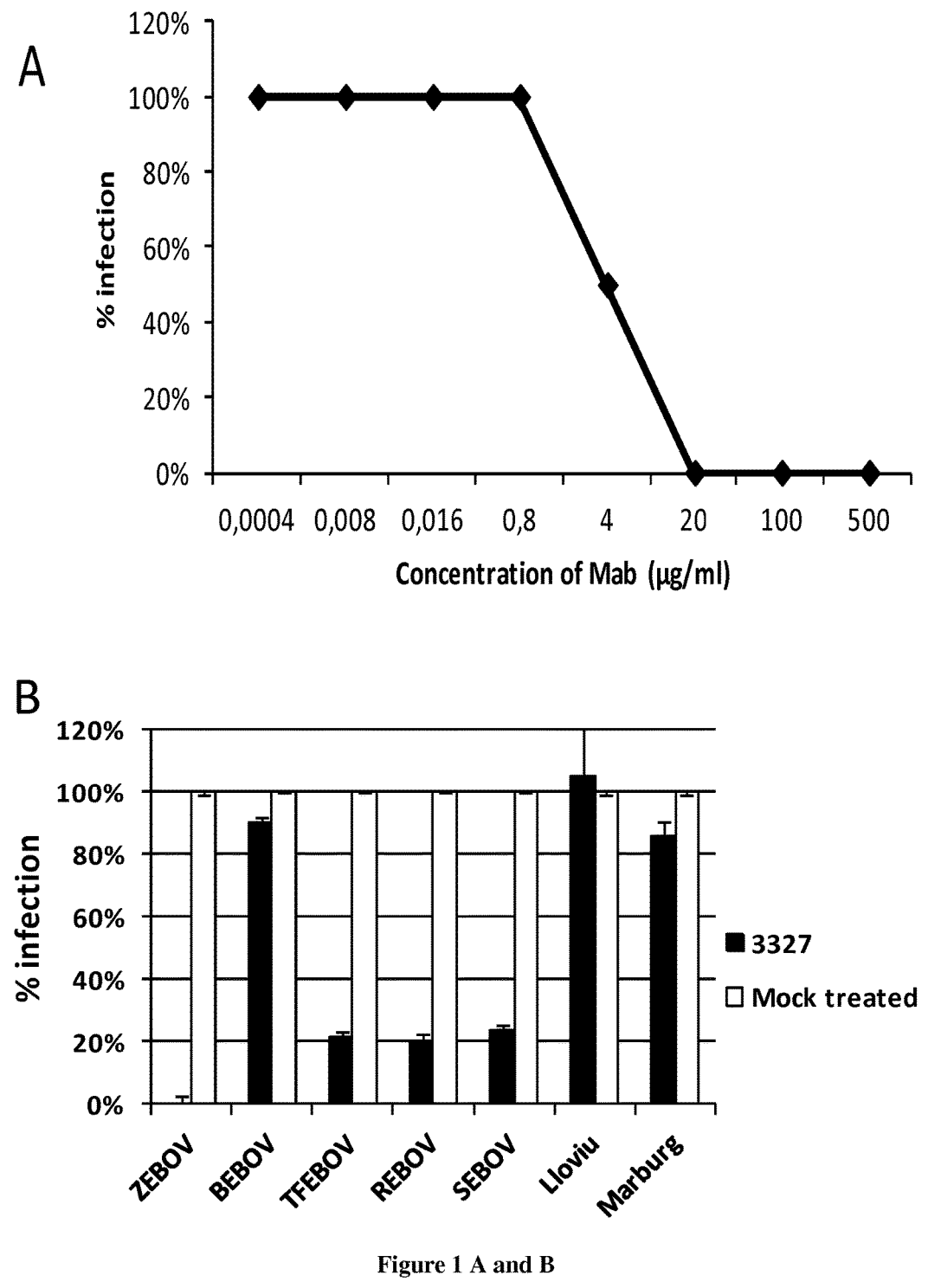

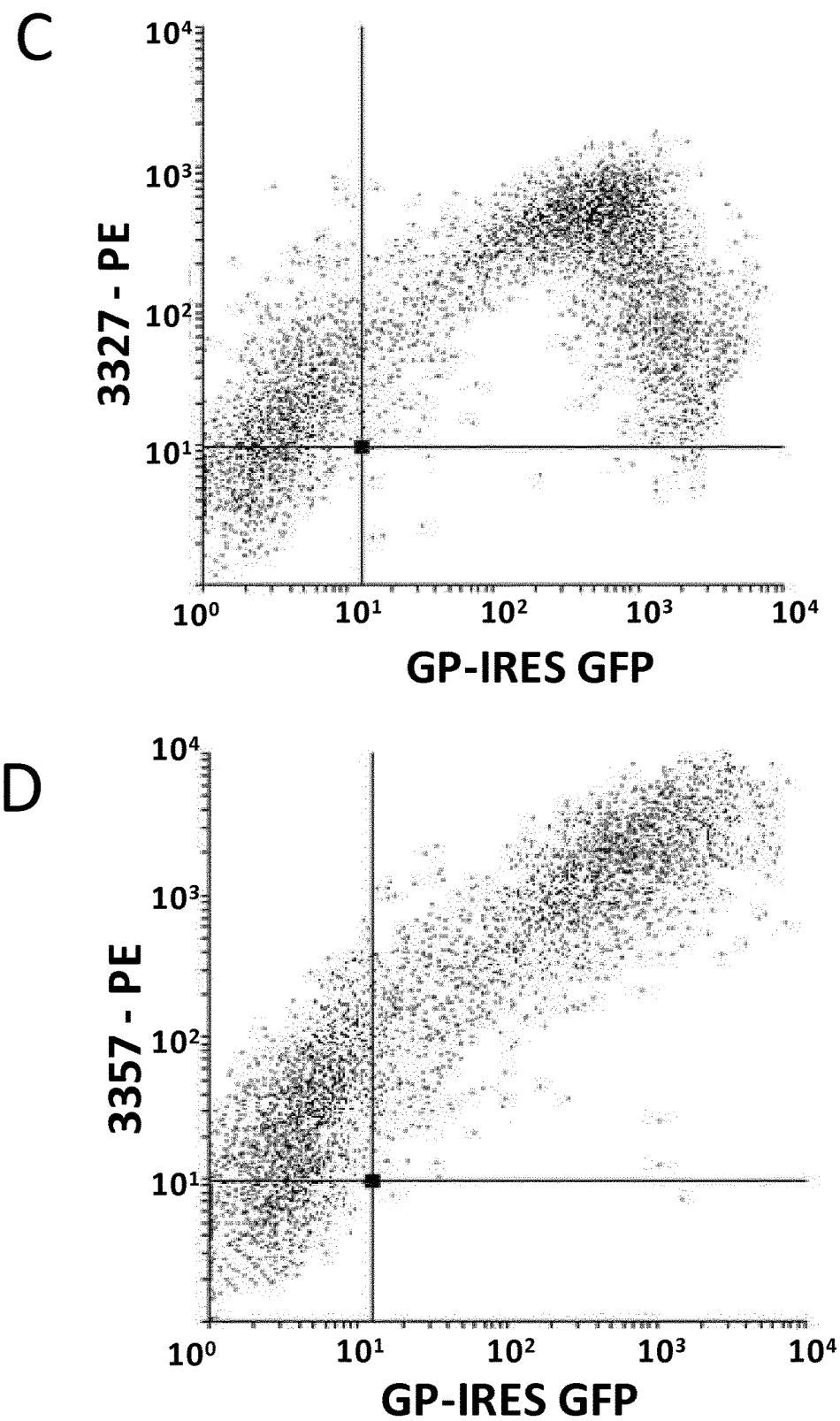
Figure 1 C and D

Figure 2:
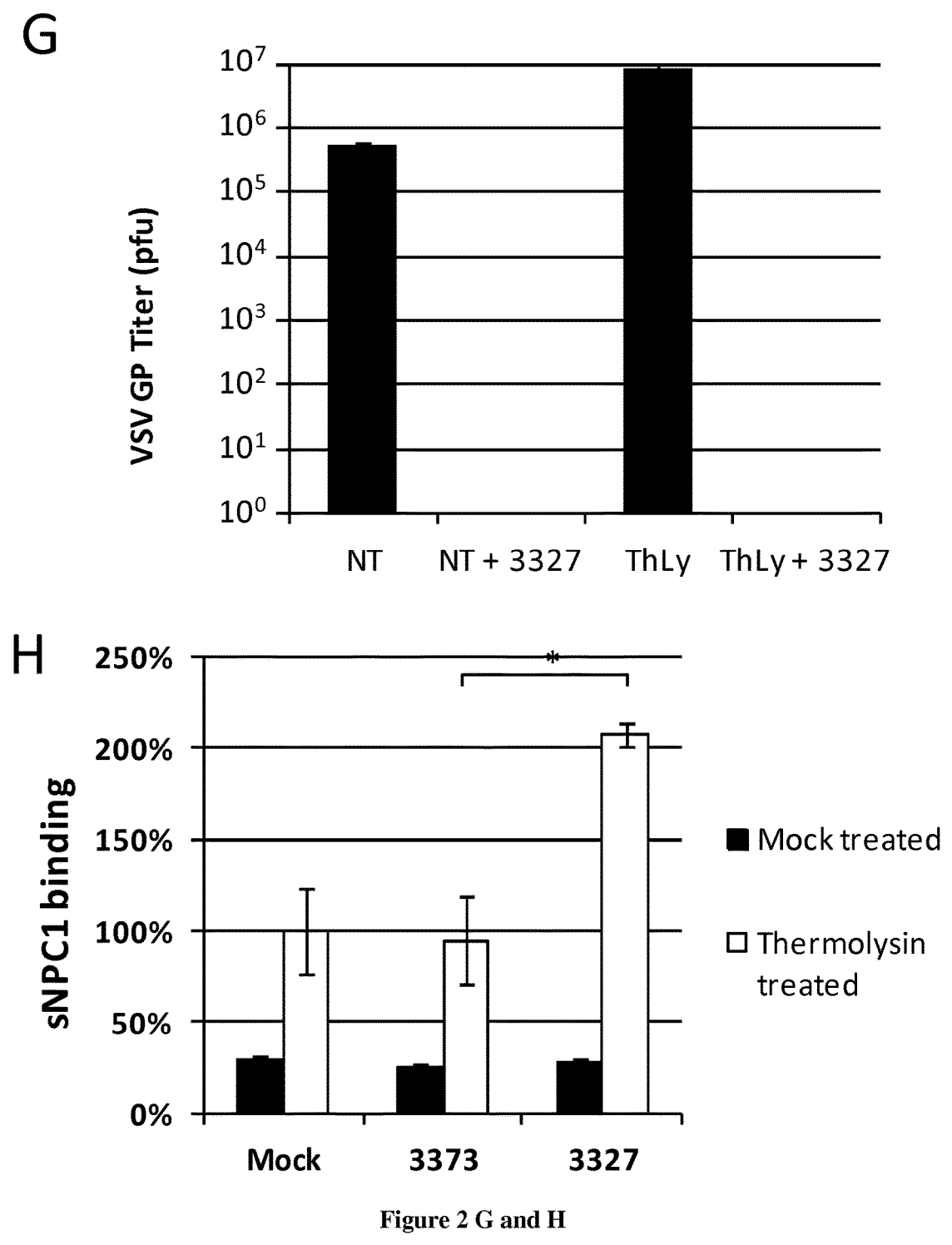

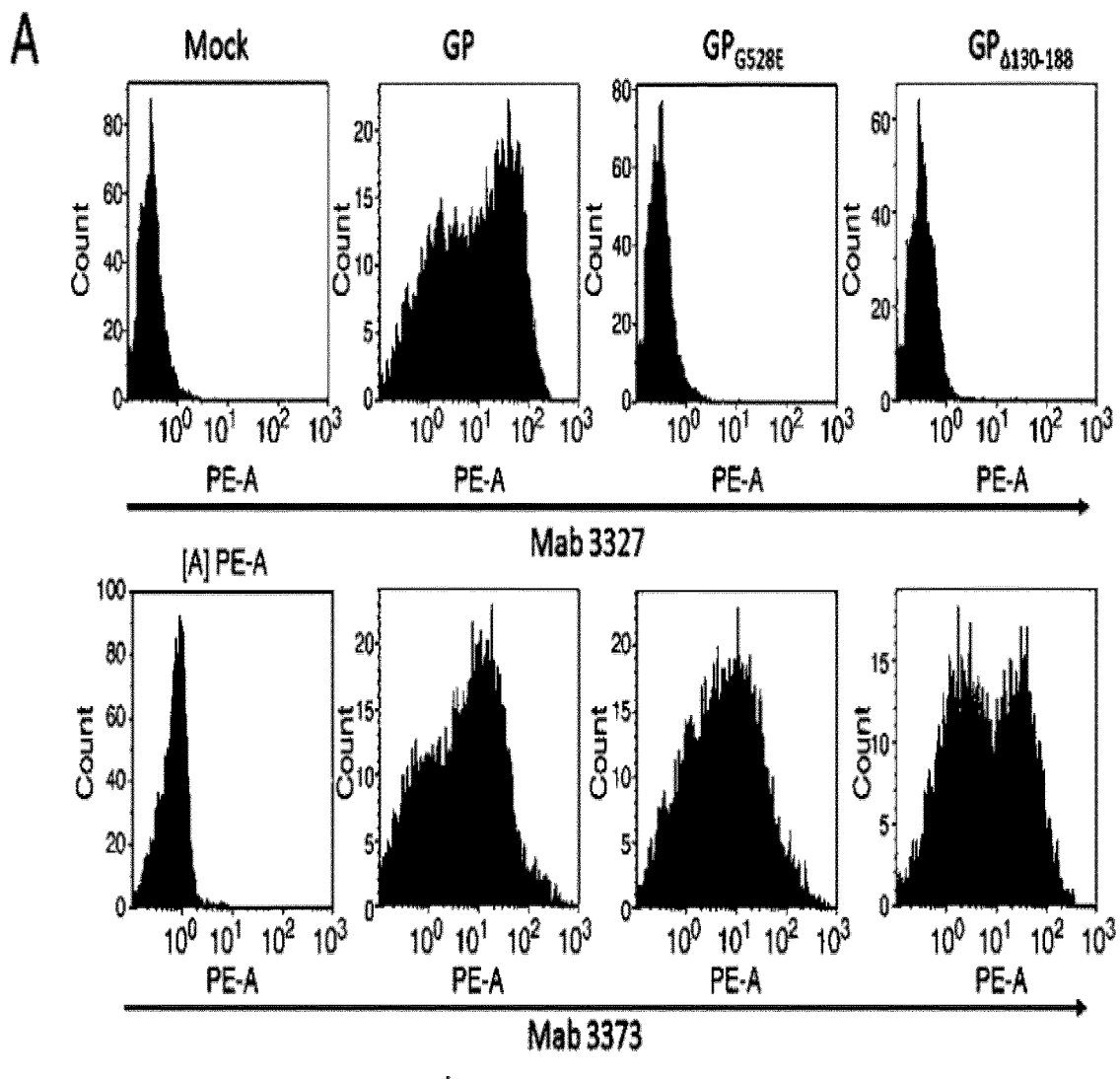
Figure 2 A and B

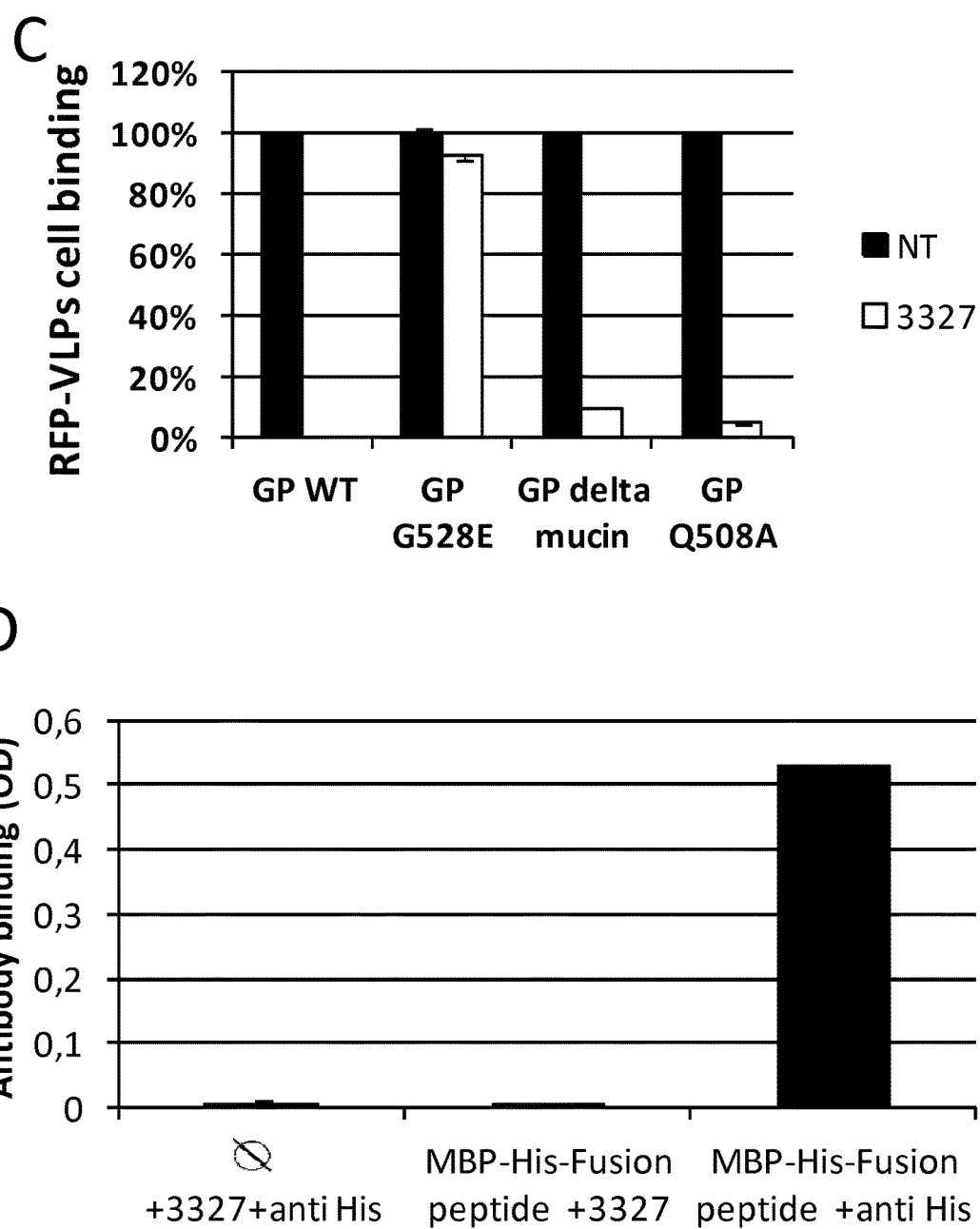
Figure 2 C and D

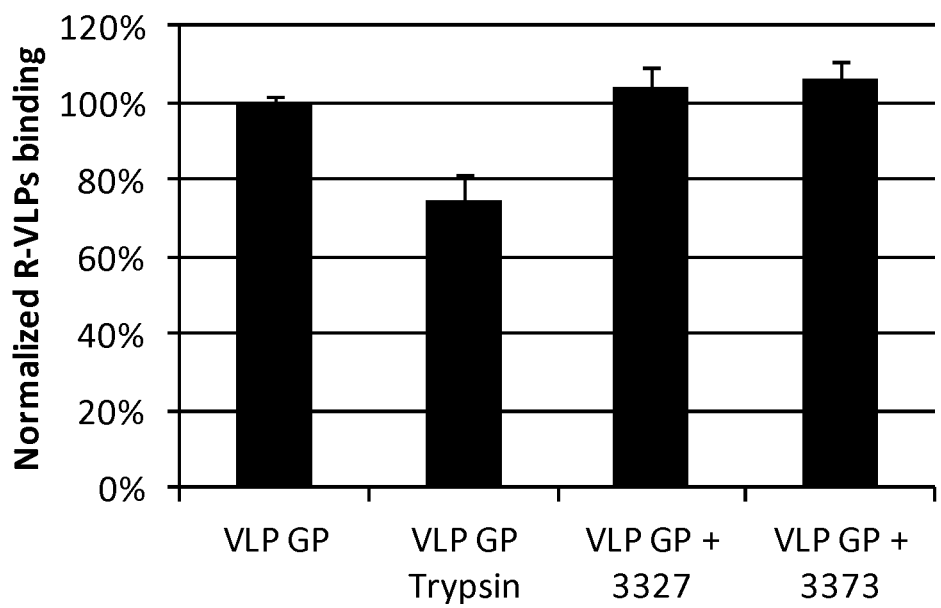
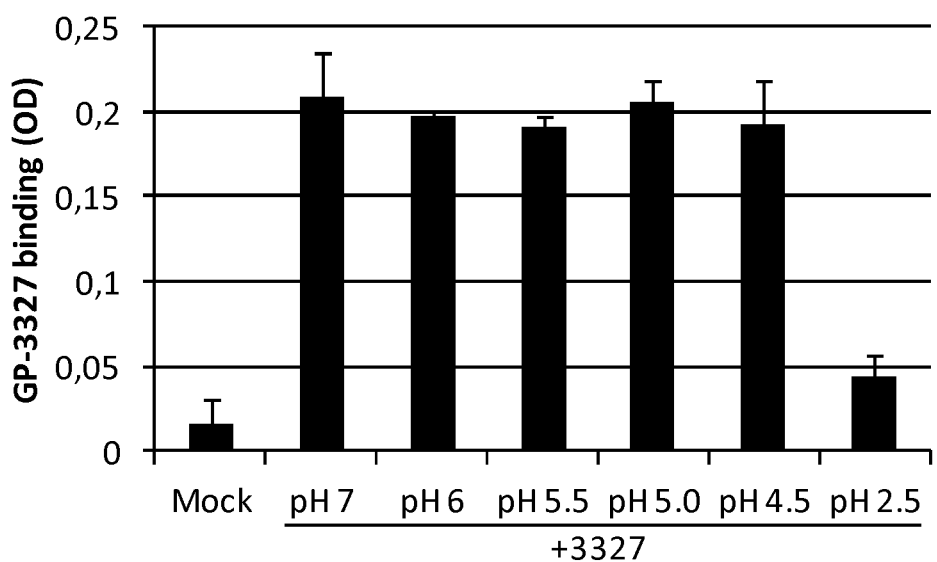
Figure 2 E and F

Figure 2 G and H

ANTIBODIES SPECIFIC TO GLYCOPROTEIN (GP) OF *EBOLAVIRUS* AND USES FOR THE TREATMENT AND DIAGNOSIS OF EBOLA VIRUS INFECTION

FIELD OF THE INVENTION

The present invention relates to antibodies or fragments thereof that specifically bind to glycoprotein (GP) of Ebolavirus, and to their use for treating and diagnosing Ebolavirus infection.

BACKGROUND OF THE INVENTION

Ebolaviruses together with Marburgviruses form the family Filoviridae, a group of enveloped negative-strand RNA viruses responsible for severe hemorrhagic fevers in humans. Currently there are no effective vaccines or antiviral treatments available for human use. The Ebolavirus genome is about 19 kb long and encodes seven structural and several nonstructural proteins [1]. The single spike glycoprotein (GP) of Ebolaviruses is responsible for both cell targeting and virus entry [2] and thus is an important target of virus neutralizing antibodies [2]. Viral cell entry occurs through initial virus attachment to different cell-surface lectins recognizing highly N- and O-glycosylated GP [3, 4], followed by endocytosis via macropinocytosis [5] and proteolytic digestion of GP by cellular proteases cathepsin B and cathepsin L [6], leading to subsequent liberation of the receptor binding domain that interacts with an intracellular receptor, the Niemann Pick C1 protein (NPC1), an endo/lysosomal transporter of cholesterol [7]. It is generally accepted that conformational rearrangements associated with the interaction between NPC1 and the cleaved GP result in exposure of a fusion loop that facilitates membrane fusion and the liberation of the viral nucleocapsid into the cell cytoplasm [8]. Recently, several putative mechanisms were proposed to explain antibody-mediated neutralization of Ebolavirus [8, 9], including either inhibition of GP cleavage by cathepsins or the prevention of membrane fusion [9]. Although the protective efficacy of immune sera from survivors or of different cocktails of anti-GP antibodies varies in different publications [10-12], there is growing interest in the development of therapies against Ebola based on anti-GP antibodies, especially given the ongoing Ebola crisis in west Africa [13].

Previously we have presented data on a panel of 87 monoclonal antibodies (mAbs) directed against Ebola Zaire (EBOV) GP [14]. One such mAb, #3327, was found to display strong ebolavirus-neutralizing activity. In this current study we map the putative GP epitope recognized by this mAb, investigate the interaction between #3327 and GP and propose the mechanism involved in its neutralizing activity.

SUMMARY OF THE INVENTION

The inventors provide an antibody that specifically binds to glycoprotein (GP) of Ebolavirus species, and demonstrate that said antibody is able to reduce the pathological Ebolavirus infection. The present invention thus provides a publicly available source for said antibody, hereinafter designated "3327" which is able to bind to glycoprotein (GP) of Ebolavirus species but also to thermolysin digested form of said EBOV GP (Shed GP). Furthermore unlike the other known neutralizing antibodies directed to GP of Ebolavirus species (KZ52, c2g4, c4g7, 16F6, JP3K11), mAb 3327 is not sensitive to GP escape mutation Q508A and shows strong neutralization ability (SN50 1-4 µg/m) on Zaïre Ebolavirus strain but also on Sudan, Reston and Taï Forrest Ebolavirus strain. The 3327 monoclonal antibody is able to bind cell surface (plasma membrane) GP but unable to recognize GP in denaturing conditions. This together with the distribution of key residues for its binding over GP1 (130-188) and GP2 (fusion peptide) allows to conclude that this antibody recognizes a conformational epitope, and is able to neutralize Ebolavirus by blocking the translocation of its genetic material in the cytosol.

DETAILED DESCRIPTION OF THE INVENTION

Definitions:

In order that the present invention may be more readily understood, certain terms are first defined. Additional definitions are set forth throughout the detailed description.

The term "Ebola virus" has its general meaning in the art and refers to a virus member of the family Filoviridae, a group of enveloped, negative-strand RNA viruses responsible for severe hemorrhagic fevers in humans and other mammals, known as Ebola virus disease (EVD). Ebola virus has caused the majority of human deaths from EVD, and is the cause of the 2013-2014 Ebola virus epidemic in West Africa, which has resulted in at least 22,091 suspected cases and 8,810 confirmed deaths (see http://en.wikipedia.org/wiki/Ebola_virus). Ebola virus (EBOV) is one of five known viruses within the genus Ebolavirus. The genus Ebolavirus is a virological taxon included in the family Filoviridae, order Mononegavirales. The members of this genus are called ebolaviruses. The five known virus species are named for the region where each was originally identified: Bundibugyo Ebolavirus, Reston Ebolavirus, Sudan Ebolavirus, Taï Forest Ebolavirus (originally Cô d'Ivoire Ebolavirus), and Zaire Ebolavirus. The EBOV genome is about 19 kb long and codes for seven structural proteins and at least two nonstructural proteins.

The term "glycoprotein of Ebolavirus" also called hereafter "EBOV GP" or "GP" has its general meaning in the art and refers to single spike glycoprotein (GP) of EBOV which is responsible for cell targeting and virus entry (ref 8). GP bears a signal peptide at the N terminus, which targets the protein to the endoplasmic reticulum (GPer). Glycosylation in the endoplasmic reticulum (ER) and later in the Golgi apparatus contributes to approximately half of the mass of GP, with O-linked glycans conferring a mucin-like property to the C terminus of the GP1 subunit (Feldmann, H., et al 2001 J. Gen. Virol. 82; Volchkov, et al. 2005. Adv. Virus Res. 64). Mature GP represents a complex of the disulfide-linked subunits GP1 and GP2 (Volchkov, V. E. et al. 1998. PNAS 95). Unless specified otherwise, the term GP corresponds to the mature form of plasma membrane GP, including disulphide linked subunits GP1 and GP2, wherein GP1 subunit corresponds to residues 34-500 of SEQ ID NO:18 and GP2 subunit corresponds to residues 501-676 of SEQ ID NO:18

According to the present invention, "antibody" or "immunoglobulin" have the same meaning, and will be used equally in the present invention. The term "antibody" as used herein refers to immunoglobulin molecules and immunologically active portions of immunoglobulin molecules, i.e., molecules that contain an antigen binding site that immunospecifically binds an antigen, or single chains thereof. As such, the term antibody encompasses not only whole antibody molecules, but also antibody fragments as well as variants (including derivatives) of antibodies, antibody fragments, and fusion protein comprising an antigen-binding portion of an antibody.

In naturally occurring antibodies, two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have each three CDRs, designated LCDR1, LCDR2, LCDR3 and HCDR1, HCDR2, HCDR3, respectively. An antigen-binding site, therefore, typically includes six CDRs, comprising the CDRs set from each of a heavy and a light chain V region. Framework Regions (FRs) refer to amino acid sequences interposed between CDRs. Each VH and VL is composed of three CDRs and four FRs arranged from amino-terminus to carboxy-terminus in the following order: FR1, CDR1, FR2, CDR2, FR3, CDR3, FR4.

Furthermore, although the two domains of the Fv fragment, VL and VH, are coded for by separate genes, they can be joined, using recombinant methods, by a synthetic linker that enables them to be made as a single chain protein in which the VL and VH regions pair to form monovalent molecules (known as single chain Fv (scFv); see e.g., Bird et al., 1988 Science 242:423-426; and Huston et al., 1988 Proc. Natl. Acad. Sci. 85:5879-5883). Such single chain antibodies are also intended to be encompassed within the term "antigen-binding portion" of an antibody. These antibody fragments are obtained using conventional techniques known to those of skill in the art, and the fragments are screened for utility in the same manner as are intact antibodies.

An "isolated antibody", as used herein, refers to an antibody that is substantially free of other antibodies having different antigenic specificities (e.g., an isolated antibody that specifically binds to a conformational epitope of GP is substantially free of antibodies that specifically bind to other distinct epitopes of GP or epitopes on distinct proteins). An isolated antibody that specifically binds to a conformational epitope of GP may, however, have cross-reactivity to other antigens, such as similar conformational epitopes of GP proteins from other Ebolavirus species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutant versions of human germline sequences or antibody containing consensus framework sequences derived from human framework sequences analysis.

The term "recombinant antibody", as used herein, includes all antibodies that are prepared, expressed, created or isolated by recombinant means, such as antibodies isolated from an animal (e.g., a mouse) or a hybridoma prepared therefrom, antibodies isolated from a host cell transformed to express the antibody, e.g., from a transfectoma, antibodies isolated from a recombinant, combinatorial antibody library, and antibodies prepared, expressed, created or isolated by any other means that involve splicing of all or a portion of a immunoglobulin gene, sequences to other DNA sequences.

The term "chimeric antibody" refers to an antibody which comprises a VH domain and a VL domain of a non-human antibody, and a CH domain and a CL domain of a human antibody.

According to the invention, the term "humanized antibody" refers to an antibody having variable region framework and constant regions from a human antibody but retains substantially the same CDRs of a non-human antibody.

The term "antibody fragment" refers to a fragment of an antibody which contains the variable domains comprising the CDRs of said antibody. The basic antibody fragments include Fab, Fab', F(ab')2 Fv, scFv, dsFv, diabodies, tribodies, or tetrabodies and the like. For example of antibody fragment see also for review, Holliger et al Nature Biotechnology 23, issue 9 1126-1136 (2005), which is included herein by reference.

The term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

The term "F(ab')2" refers to an antibody fragment having a molecular weight of about 100,000 and antigen binding activity, which is slightly larger than the Fab bound via a disulfide bond of the hinge region, among fragments obtained by treating IgG with a protease, pepsin.

The term "Fab'" refers to an antibody fragment having a molecular weight of about 50,000 and antigen binding activity, which is obtained by cutting a disulfide bond of the hinge region of the F(ab')2.

A single chain Fv ("scFv") polypeptide is a covalently linked VH::VL heterodimer which is usually expressed from a gene fusion including VH and VL encoding genes linked by a peptide-encoding linker. "dsFv" is a VH::VL heterodimer stabilised by a disulfide bond. Divalent and multivalent antibody fragments can form either spontaneously by association of monovalent scFvs, or can be generated by coupling monovalent scFvs by a peptide linker, such as divalent sc(Fv)2.

The term "diabodies" "tribodies" or "tetrabodies" refers to small antibody fragments with multivalent antigen-binding sites (2, 3 or four), which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

As used herein, "neutralizing antibody" refers to an antibody, for example, a monoclonal antibody, capable of disrupting a formed viral particle or inhibiting formation of a viral particle or prevention of binding to or infection of mammalian cells by a viral particle, or prevention of translocation of genetic material into the cytosol of infected cells. In a specific embodiment, a neutralizing antibody refers to an antibody that has an SN50 of at least 100 µg/ml or below, preferably at least 50 µg/ml or below, more preferably at least 10 µg/ml or below, as measured in a seroneutralization assay as described in more detail in the Examples below.

By "purified" and "isolated" it is meant, when referring to an antibody according to the invention or to a nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type are present. An "isolated" nucleic acid molecule which encodes a particular polypeptide refers to a nucleic acid molecule which is substantially free of other nucleic acid molecules that do not encode the polypeptide; however, the molecule may include some additional bases or moieties which do not deleteriously affect the basic characteristics of the composition.

As used herein, an antibody that binds to a "conformational epitope" of Ebolavirus glycoprotein GP, refers to an antibody that does not bind to said glycoprotein GP in an in vitro assay under denaturing conditions, for example in a Western blot. In specific embodiments, the antibody of the invention binds to a conformational epitope comprising residues in both GP1 and GP2 subunits.

Antibody binding to EBOV GP can be assayed by conventional methods known in the art. The mature form of EBOV GP is preferably used for assaying antibody binding to a conformational epitope of EBOV GP. Alternatively, any variant form of GP that retains binding of mAb 3327 can be used. Many different competitive binding assay format(s) can be used for determining epitope binding. The immunoassays which can be used include, but are not limited to, competitive assay systems using techniques such as radioimmunoassays, ELISA, "sandwich" immunoassays, immunoprecipitation assays, fluorescent immunoassays, protein A immunoassays, and complement-fixation assays. Such assays are routine and well known in the art (see, e.g., Ausubel et al., eds, 1994 Current Protocols in Molecular Biology, Vol. 1, John Wiley & sons, Inc., New York). For example, the BIACORE® (GE Healthcare, Piscaataway, N.J.) is one of a variety of surface plasmon resonance assay formats that are routinely used to epitope bin panels of monoclonal antibodies. Additionally, routine cross-blocking assays such as those described in Antibodies, A Laboratory Manual, Cold Spring Harbor Laboratory, Ed Harlow and David Lane, 1988, can be performed. An example of a suitable ELISA assay is also described in the Example below.

As used herein, the term "Affinity" refers to the strength of interaction between antibody and antigen at single antigenic sites. Within each antigenic site, the variable region of the antibody "arm" interacts through weak non-covalent forces with the antigen at numerous sites; the more interactions, the stronger the affinity. Affinity can be determined by measuring $K_D$. The term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of an antibody is by using surface plasmon resonance, or using a biosensor system such as a Biacore® system.

As used herein, "protease digested form of Ebolavirus glycoprotein GP" refers to thermolysin digested form of GP as described by Chandran et al (11) and in the Examples below.

As used herein, "escape mutation Q508A" is a mutation that has been shown to confer resistance to prior art neutralizing antibodies. A remarkable feature of the antibodies of the present invention is that they are neutralizing with mutant strains comprising GP with escape mutation Q508A.

As used herein, the percent identity between two sequences is a function of the number of identical positions shared by the sequences (i. e., % identity=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described below.

The percent identity between two amino acid sequences can be determined using the algorithm of E. Myers and W. Miller (Comput. Appl. Biosci. 4: 1 1-17, 1988) which has been incorporated into the ALIGN program. In addition, the percent identity between two amino acid sequences can be determined using the Needleman and Wunsch (J. Mol. Biol. 48:443-453, 1970) algorithm which has been incorporated into the GAP program in the GCG software package. Yet another program to determine percent identity is CLUSTAL (M. Larkin et al., Bioinformatics 23:2947-2948, 2007; first described by D. Higgins and P. Sharp, Gene 73:237-244, 1988) which is available as stand-alone program or via web servers (see http://www.clustal.org/).

The percent identity between two nucleotide amino acid sequences may also be determined using for example algorithms such as the BLASTN program for nucleic acid sequences using as defaults a word length (W) of 11, an expectation (E) of 10, M=5, N=4, and a comparison of both strands.

The terms "cross-block", "cross-blocked" and "cross-blocking" are used interchangeably herein to mean the ability of an antibody or other binding agent to interfere with the binding of other antibodies or binding agents to EBOV GP in a standard competitive binding assay.

The ability or extent to which an antibody is able to interfere with the binding of another antibody or binding molecule to EBOV GP, and therefore whether it can be said to cross-block according to the invention, can be determined using standard competition binding assays. One suitable assay involves the use of the Biacore technology (e.g. by using the BIAcore 3000 instrument (Biacore, Uppsala, Sweden)), which can measure the extent of interactions using surface plasmon resonance technology. Another assay for measuring cross-blocking uses an ELISA-based approach as described in the Example (see Section 1 of the Example).

For example, an antibody is defined as cross-blocking in an ELISA assay, if the solution phase anti-GP antibody is able to cause a reduction of between 60% and 100%, specifically between 70% and 100%, and more specifically between 80% and 100%, of the GP detection signal (i.e. the amount of GP bound by the coated antibody) as compared to the GP detection signal obtained in the absence of the solution phase anti-GP antibody (i.e. the positive control wells).

Isolated Antibody mAb 3327

The inventors have cloned and sequenced the variable domain (VL) of the light chain, and the variable domain (VH) of the heavy chain of the murine monoclonal antibody 3327. The location of the sequences encoding the complementarity determining regions (CDRs) of said antibody have been determined with reference to other antibody sequences (Kabat EA et al., 1991). This system is set forth in Kabat et al., 1987, in Sequences of Proteins of Immunological Interest, US Department of Health and Human Services, NIH, USA (hereafter "Kabat et al."). This numbering system is used in the present specification. The Kabat residue designations do not always correspond directly with the linear numbering of the amino acid residues in SEQ ID sequences. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence. The CDRs of the heavy chain variable domain are located at residues 31-35B (H-CDR1), residues 50-65 (H-CDR2) and residues 95-102 (H-CDR3) according to the Kabat numbering system. The CDRs of the light chain variable domain are located at residues 24-34 (L-CDR1), residues 50-56 (L-CDR2) and residues 89-97 (L-CDR3) according to the Kabat numbering system.

These sequences derived from mAb 3327 are described below in Table 1 (for the heavy chain) and Table 2 (for the light chain).

TABLE 1

| mAb 3327 Domains | DNA Sequence | Aminoacid Sequence |
|---|---|---|
| VH | GAGGTGCAGCTTCAGGAGTCAGGACCTAGCCTCGG GAAACCTTCTCAGACTCTGTCCCTCACCTGTTCTGTC ACTGGCGACTCCATCACCAGTGGTTACTGGAACTGG ATCCGGAAATTCCCAGGGAGTAAGCTTGAGTACATG GGGTACATAACCTCCAGTGGTAGCACTTACTACAAT CCATCTCTCAAAAGTCGCATCTCCATCACTCGAGAC ACATCCAAGAACCAGTATTACCTGCAGTTGAATTCT GTGACTTCTGAGGACACAGCCACCTATTACTGTGCA AGAGAAGGGGCCCGATCATCCGGGGGCTGGTACTT CGATGTCTGGGGCGCAGGGACCACGGTCACCGTCTC CTCA (SEQ ID NO: 1) | EVQLQESGPSLGKPSQTLSLTCSVTGD SITSGYWNWIRKFPGSKLEYMGYITSS GSTYYNPSLKSRISITRDTSKNQYYLQ LNSVTSEDTATYYCAREGARSSGGW YFDVWGAGTTVTVSS (SEQ ID NO: 5) |
| VH-CDR1 | GGCGACTCCATCACCAGTGGTTACTGGAAC (SEQ ID NO: 2) | GDSITSGYWN (SEQ ID NO: 6) |
| VH-CDR2 | TACATAACCTCCAGTGGTAGCACTTACTACAATCCA TCTCTCAAAAGT (SEQ ID NO: 3) | YITSSGSTYYNPSLKS (SEQ ID NO: 7) |
| VH-CDR3 | GAAGGGGCCCGATCATCCGGGGGCTGGTACTTCGAT GTC SEQ ID NO: 4) | EGARSSGGWYFDV (SEQ ID NO: 8) |

TABLE 2

| mAb 3327 Domains | DNA Sequence | Aminoacid Sequence |
|---|---|---|
| VL | GACATTGTGATGACCCAGTCTCACAAATTCAT GTCCACATCAGTAGGAGACAGGGTCAGCATCA CCTGCAAGGCCAGTCAGGATGTGAGTTCTGCT GTAGTTTGGTATCAACAAAAACCAGGGCAATC TCCTAAACTACTGATTTACTGGGCATCCACCC GGCACACTGGAGTCCCTGATCGCTTCACAGGC AGTGGATCTGGGACAGATTATACTCTCACCAT CAGCAGTGTGCAGGCTGAAGACCTGGCACTTT ATTACTGTCAGCAACATTATAGCACTCCGACG TTCGGTGGAGGCACCAAGCTGGAAATCAAAC GGGCT (SEQ ID NO: 9) | DIVMTQSHKFMSTSVGDRVSITCKASQDV SSAVVWYQQKPGQSPKLLIYWASTRHTG VPDRFTGSGSGTDYTLTISSVQAEDLALYY CQQHYSTPTFGGGTKLEIKRA (SEQ ID NO: 13) |
| VL-CDR1 | AAGGCCAGTCAGGATGTGAGTTCTGCTGTAGT T (SEQ ID NO: 10) | KASQDVSSAVV (SEQ ID NO: 14) |
| VL-CDR2 | TGGGCATCCACCCGGCACACT (SEQ ID NO: 11) | WASTRHT (SEQ ID NO: 15) |
| VL-CDR3 | CAGCAACATTATAGCACTCCGACG (SEQ ID NO: 12) | QQHYSTPT (SEQ ID NO: 16) |

The present invention thus relates to an antibody characterized in that it binds to a conformational epitope of glycoprotein (GP) of Ebola virus and in that it comprises a heavy chain having the VH-CDR1 as set forth in SEQ ID NO:6, VH-CDR2 as set forth in SEQ ID NO:7 and VH-CDR3 as set forth in SEQ ID NO: 8 and a light chain having the VL-CDR1 as set forth in SEQ ID NO:14, VL-CDR2 as set forth in SEQ ID NO:15 and VL-CDR3 as set forth in SEQ ID NO:16.

Other antibodies of the invention include those having amino acids that have been mutated by amino acid deletion, insertion or substitution, yet have at least 60, 70, 80, 90, 95 or 100 percent identity in the CDR regions with the CDR regions depicted in the sequences described above. In some embodiments, the antibody of the invention is a mutant variant of any one of mAb 3327, wherein said mutant variant antibody include mutant amino acid sequences wherein no more than 1, 2, 3, 4 or 5 amino acids have been mutated by amino acid deletion, insertion or substitution in the CDR regions when compared with the CDR regions depicted in the sequences described above.

Accordingly, the invention also provides an antibody comprising a heavy chain and/or a light chain of antibody 3327 wherein:
the VL domain having at least 70, 71; 72; 73; 74; 75; 76; 77; 78; 79; 80; 81; 82; 83; 84; 85; 86; 87; 88; 89; 90; 91; 92; 93; 94; 95; 96; 97; 98; 99 or 100% identity with the VL domain of the antibody 3327 (SEQ ID N:13), and
the VH domain having at least 70, 71; 72; 73; 74; 75; 76; 77; 78; 79; 80; 81; 82; 83; 84; 85; 86; 87; 88; 89; 90; 91; 92; 93; 94; 95; 96; 97; 98; 99 or 100% identity with the VH domain of the antibody 3327 (SEQ ID N:5).
that binds to glycoprotein (GP) of Ebola virus with substantially the same affinity as an antibody having a variable light chain domain (VL) and/or a variable heavy chain domain (VH) of the antibody 3327.

In another specific embodiment, the invention also provides an antibody comprising a heavy chain and a light chain wherein the variable domains comprise:
a VH-CDR1 having at least 90; 91; 92; 93; 94; 95; 96; 97; 98; 99 or 100% identity with the VH-CDR1 of the VH chain of the antibody 3327 and/or,
a VH-CDR2 having at least 90; 91; 92; 93; 94; 95; 96; 97; 98; 99 or 100% identity with the VH-CDR2 of the VH chain of the antibody 3327 and/or,
a VH-CDR3 having at least 90; 91; 92; 93; 94; 95; 96; 97; 98; 99 or 100% identity with the VH-CDR3 of the VH chain of the antibody 3327 and/or,
a VL-CDR1 having at least 90; 91; 92; 93; 94; 95; 96; 97; 98; 99 or 100% identity with the VL-CDR1 of the VL chain of the antibody 3327 and/or,
a VL-CDR2 having at least 90; 91; 92; 93; 94; 95; 96; 97; 98; 99 or 100% identity with the VL-CDR2 of the VL chain of the antibody 3327 and/or,
a VL-CDR3 having at least 90; 91; 92; 93; 94; 95; 96; 97; 98; 99 or 100% identity with the VL-CDR3 of the VL chain of the antibody 3327,
that specifically binds to glycoprotein (GP) of Ebola virus with substantially the same affinity as an antibody having a variable light chain domain (VL) comprising the VL-CDR1, VL-CDR2 and VL-CDR3 of the VL domain and/or a variable heavy chain domain (VH) comprising the VH-CDR1, VH-CDR2 and VH-CDR3 of the VH domain of the antibody 3327, and more preferably with substantially the same affinity as the antibody 3327.

Yet other antibodies of the invention include antibodies selected from the group consisting of:
(i) an antibody comprising a heavy chain having the VH-CDR1 as set forth in SEQ ID NO:6, VH-CDR2 as set forth in SEQ ID NO:7 and VH-CDR3 as set forth in SEQ ID NO: 8 and a light chain having the VL-CDR1, CDR1 as set forth in SEQ ID NO:14, VL-CDR2 as set forth in SEQ ID NO:15 and VL-CDR3 as set forth in SEQ ID NO:16;
(ii) a murine antibody which comprises the VL domain of SEQ ID NO:5 and the VH domain of SEQ ID NO:13;
(iii) a chimeric or humanized antibody obtained from the antibody of ii); and,
(iv) the antigen-binding fragments of any of the antibodies i) to iii) above.

In another embodiment the antibody of the invention comprises the VL domain and the VH domain of the antibody 3327.

In another embodiment, the antibody of the invention is a chimeric antibody, which comprises the variable domains (VL and VH) of the antibody 3327.

In another embodiment, the antibody of the invention is a humanized antibody comprising the CDRs of the antibody 3327.

Homologous Antibodies

In yet another embodiment, an antibody has full length heavy and light chain amino acid sequences; full length heavy and light chain nucleotide sequences, variable region heavy and light chain nucleotide sequences, or variable region heavy and light chain amino acid sequences, or all 6 CDR regions amino acid sequences or nucleotide coding sequences that are homologous to the amino acid or nucleotide sequences of the antibody mAb 3327 described above, in particular in Table 1 and Table 2, and wherein the antibodies retain the desired functional properties of the original antibody mAb 3327, in particular, it binds to a conformational epitope of Ebolavirus glycoprotein GP, and it has an SN50 of at least 10 µg/ml or below, as measured in a seroneutralization assay with Zaire Ebolavirus.

The homologous antibodies preferably exhibit one or more additional desired functional properties of the original mAb 3327 selected from the group consisting of:
(i) it binds to protease digested form of Ebolavirus glycoprotein GP;
(ii) it further neutralizes Sudan, Reston and Taï Forrest Ebolavirus species;
(iii) it does not bind to a mutant GP having G528E amino acid mutation; and/or,
(iv) it neutralizes mutant strain of Ebola virus having GP with escape mutation Q508A.

For example, the invention relates to homologous antibodies of mAb 3327 (or a binding protein comprising an antigen binding portion thereof), comprising a variable heavy chain ($V_H$) and a variable light chain ($V_L$) sequences where the CDR sequences, i.e. the 6 CDR regions; HCDR1, HCDR2, HCDR3, LCDR1, LCDR2, LCDR3, share at least 60, 70, 90, 95 or 100 percent sequence identity to the corresponding CDR sequences of antibody of mAb 3327 as defined in Tables 1 and 2, wherein said homologous antibody binds to a conformational epitope of Ebolavirus glycoprotein GP, and the homologous antibody exhibits at least one or more of the following functional properties:
(i) it has an SN50 of at least 10 µg/ml or below, as measured in a seroneutralization assay with Zaire Ebolavirus,
(ii) it binds to thermolysin digested form of Ebolavirus glycoprotein GP;

(iii) it further neutralizes Sudan, Reston and Taï Forrest Ebolavirus species;
(iv) it does not bind to a mutant GP having G528E amino acid mutation; and/or,
(v) it neutralizes mutant strain of Ebolavirus having GP with escape mutation Q508A.

The invention further relates to homologous antibodies of mAb 3327 (or a binding protein comprising an antigen binding portion thereof), comprising a variable heavy chain ($V_H$) and a variable light chain ($V_L$) sequences where the VH and VL amino acid sequences share at least 70, 80, 90, 95 or 100 percent sequence identity to the corresponding VH and VL amino acid sequences of antibody of mAb 3327 as defined in Tables 1 and 2, wherein said homologous antibody binds to a conformational epitope of Ebolavirus glycoprotein GP, and the antibody exhibits at least one or more of the following functional properties:
(i) it has an SN50 of at least 10 µg/ml or below, as measured in a seroneutralization assay with Zaire Ebolavirus,
(ii) it binds to thermolysin digested form of Ebolavirus glycoprotein GP;
(iii) it further neutralizes Sudan, Reston and Taï Forrest Ebolavirus species;
(iv) it does not bind to a mutant GP having G528E amino acid mutation; and/or,
(v) it neutralizes mutant strain of Ebola virus having GP with escape mutation Q508A.

In various embodiments, the antibody may exhibit one or more, two or more, three or more, or four or all of the desired functional properties discussed above.

The antibody mAb 3327 has also been shown to prevent the translocation of genetic material of Ebolavirus in infected cells. In particular, this can be derived by the fact that mAb 3327 is internalized into the cells after infection but remain in the endosome, as it can be visualized by fluorescence detection of the antibody after incubation with cells and Ebolavirus virions. Alternatively, this can also be derived by the fact mAb 3327 is unable to prevent the binding of thermolysin digested GP EBOV on soluble NPC1 loop C, but in fact, mAb 3327 increase the binding of NPC1 to thermolysin treated GP EBOV.

Accordingly, in specific embodiments, the homologous antibodies of the invention are capable of increasing the binding of NPC1 to thermolysin treated GP EBOV.

In certain embodiments, an antibody of the invention has a heavy chain variable region comprising HCDR1, HCDR2, and HCDR3 amino acid sequences and a light chain variable region comprising LCDR1, LCDR2, and LCDR3 amino acid sequences, wherein one or more of these CDR sequences have specified amino acid sequences based on mAb 3327 described herein or conservative modifications thereof, and wherein the antibody retains the desired functional properties of mAb 3327 as described herein.

As used herein, the term "conservative sequence modifications" is intended to refer to amino acid substitutions in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family, and the altered antibody can be tested for retained function using the functional assays described herein.

Modifications can be introduced into an antibody of the invention by standard techniques known in the art, such as site-directed mutagenesis and PCR-mediated mutagenesis.

Antibodies that Cross-block mAb 3327 and/or that Bind to the Same Epitope as mAb 3327

The antibody mAb 3327 has been shown to bind to an original epitope of glycoprotein GP, enabling specific neutralization properties. Therefore, additional antibodies can therefore be identified based on their ability to cross-compete (e.g., to competitively inhibit the binding of), in a statistically significant manner with other antibodies of the invention, for example mAb 3327, in standard GP EBOV binding assays. Test antibody may first be screened for their binding affinity to glycoprotein GP EBOV, for example from murine hybridomas, or human recombinant antibody libraries, using for example phage display technologies as described below. The ability of a test antibody to cross-compete with or inhibit the binding of antibodies of the present invention to GP EBOV demonstrates that the test antibody can compete with that antibody for binding to GP EBOV; such an antibody may, according to non-limiting theory, bind to the same or a related (e.g., a structurally similar or spatially proximal) epitope on GP EBOV as the antibody with which it competes. Examples of Biacore or Elisa-based cross-blocking assays are described in detail in the Examples.

Accordingly, in one embodiment, the invention provides an isolated antibody which cross-blocks or is cross-blocked by at least mAb 3327 or an antibody having the same 6 CDRs of mAb 3327, from binding to a conformational epitope of glycoprotein GP EBOV, wherein said antibody has an SN50 of at least 10 µg/ml or below, as measured in a seroneutralization assay with Zaire Ebolavirus.

In another embodiment, the invention provides antibodies that bind to the same conformational epitope as does mAb 3327 as described herein.

Optionally, in order to further confirm that the above-described cross-blocking antibodies have the same properties as mAb 3327, it can be further screened for one or more of the following properties of mAb 3327:
(i) it binds to thermolysin digested form of Ebolavirus glycoprotein GP;
(ii) it further neutralizes Sudan, Reston and Taï Forrest Ebolavirus species;
(iii) it does not bind to a mutant GP having G528E amino acid mutation; and/or,
(iv) it neutralizes mutant strain of Ebola virus having GP with escape mutation Q508A.

In one specific embodiment, such cross-blocking anti-GP antibody of the invention further neutralizes GP of other Ebolavirus species, including for example Sudan, Reston and Taï Forrest Ebolavirus species.

In a preferred embodiment, the antibodies of the invention are able to neutralize Ebola virus strain disease by reducing the virus replication.

The ability to neutralize Ebola Virus strain disease can easily be tested using, for instance, the neutralizing assay as described in the Example.

Nucleic Acid Molecules Encoding Antibodies of the Invention

Another aspect of the invention pertains to nucleic acid molecules that encode the antibodies of the invention. Examples of variable light chain nucleotide sequences are those encoding the variable light chain amino acid sequences of mAb 3327, the latter sequences being derived from the Table 1.

The invention also pertains to nucleic acid molecules that derive from the latter sequences having been optimized for protein expression in mammalian cells, for example, CHO cell lines, insect cells, fungal cells or bacterial cells or other available expression systems.

The nucleic acids may be present in whole cells, in a cell lysate, or may be nucleic acids in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. 1987 Current Protocols in Molecular Biology, Greene Publishing and Wiley Interscience, New York. A nucleic acid of the invention can be, for example, DNA or RNA and may or may not contain intronic sequences. In an embodiment, the nucleic acid is a cDNA molecule. The nucleic acid may be present in a vector such as a phage display vector, or in a recombinant plasmid vector.

Nucleic acids of the invention can be obtained using standard molecular biology techniques. Once DNA fragments encoding, for example, $V_H$ and $V_L$ segments are obtained, these DNA fragments can be further manipulated by standard recombinant DNA techniques, for example to convert the variable region genes to full-length antibody chain genes, to Fab fragment genes or to an scFv gene. In these manipulations, a $V_L$- or $V_H$-encoding DNA fragment is operatively linked to another DNA molecule, or to a fragment encoding another protein, such as an antibody constant region or a flexible linker. The term "operatively linked", as used in this context, is intended to mean that the two DNA fragments are joined in a functional manner, for example, such that the amino acid sequences encoded by the two DNA fragments remain in-frame, or such that the protein is expressed under control of a desired promoter.

The isolated DNA encoding the $V_H$ region can be converted to a full-length heavy chain gene by operatively linking the $V_H$-encoding DNA to another DNA molecule encoding heavy chain constant regions (CH1, CH2 and CH3). For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as to a Fab light chain gene) by operatively linking the $V_L$-encoding DNA to another DNA molecule encoding the light chain constant region, CL.

To create an scFv gene, the $V_H$- and $V_L$-encoding DNA fragments are operatively linked to another fragment encoding a flexible linker, e.g., encoding the amino acid sequence (Gly4-Ser)$_3$, such that the $V_H$ and $V_L$ sequences can be expressed as a contiguous single-chain protein, with the $V_L$ and $V_H$ regions joined by the flexible linker (see e.g., Bird et al., 1988 Science 242:423-426; Huston et al., 1988 Proc. Natl. Acad. Sci. USA 85:5879-5883; McCafferty et al., 1990 Nature 348:552-554).

Isolation of Recombinant Antibodies of the Invention

A variety of methods of screening antibodies have been described in the Art. Such methods may be divided into in vivo systems, such as transgenic mice capable of producing fully human antibodies upon antigen immunization and in vitro systems, consisting of generating antibody DNA coding libraries, expressing the DNA library in an appropriate system for antibody production, selecting the clone that express antibody candidate that binds to the target with the affinity selection criteria and recovering the corresponding coding sequence of the selected clone. These in vitro technologies are known as display technologies, and include without limitation, phage display, RNA or DNA display, ribosome display, yeast or mammalian cell display. They have been well described in the Art (for a review see for example: Nelson et al., 2010 Nature Reviews Drug discovery, "Development trends for human monoclonal antibody therapeutics" (Advance Online Publication) and Hoogenboom et al. in *Method in Molecular Biology* 178:1-37, O'Brien et al., ed., Human Press, Totowa, N.J., 2001). In one specific embodiment, human recombinant antibodies of the invention are isolated using phage display methods for screening libraries of human recombinant antibody libraries, for example, against mature form of plasma membrane EBOV GP or related GP with the same conformational epitope as recognized by mAb 3327.

Repertoires of $V_H$ and $V_L$ genes or related CDR regions can be separately cloned by polymerase chain reaction (PCR) or synthesized by DNA synthesizer and recombined randomly in phage libraries, which can then be screened for antigen-binding clones. Such phage display methods for isolating human antibodies are established in the art or described in the examples below. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

In a certain embodiment, human antibodies directed against EBOV GP can be identified using transgenic or transchromosomic mice carrying parts of the human immune system rather than the mouse system. These transgenic and transchromosomic mice include mice referred to herein as HuMAb mice and KM mice, respectively.

Monoclonal antibodies (mAbs) can alternatively be produced by a variety of techniques, including conventional monoclonal antibody methodology e.g., the standard somatic cell hybridization technique of Kohler and Milstein, 1975 Nature 256: 495. Many techniques for producing monoclonal antibody can be employed e.g., viral or oncogenic transformation of B lymphocytes.

An animal system for preparing hybridomas is the murine system. Hybridoma production in the mouse is a well-established procedure. Immunization protocols and techniques for isolation of immunized splenocytes for fusion are known in the art. Fusion partners (e.g., murine myeloma cells) and fusion procedures are also known.

Chimeric or humanized antibodies of the present invention can also be prepared based on the sequence of a murine monoclonal antibody prepared as described above, such as for example mAb 3327 and its functional fragments or its variants obtained by CDR-grafting. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art. See e.g., U.S. Pat. No. 5,225,539 to Winter, and U.S. Pat. Nos. 5,530,101; 5,585,089; 5,693,762 and 6,180,370 to Queen et al.

To generate hybridomas producing monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific or epitope-specific antibodies.

Methods of Producing Antibodies of the Invention:

The antibodies of the invention may be produced by any technique known in the art, such as, without limitation, any chemical, biological, genetic or enzymatic technique, either alone or in combination.

Knowing the amino acid sequence of the desired sequence, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies of the invention can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

Accordingly, a further object of the invention relates to a nucleic acid encoding an antibody according to the invention.

In a particular embodiment, the invention relates to a nucleic acid encoding the VH domain of the antibody of the invention (3327) and/or the VL domain of the antibody of the invention (3327).

Typically, said nucleic acid is a DNA or RNA molecule, which may be included in any suitable vector, such as a plasmid, cosmid, episome, artificial chromosome, phage or a viral vector.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

So, a further object of the invention relates to a vector comprising a nucleic acid of the invention. Such vectors may comprise regulatory elements, such as a promoter, enhancer, terminator and the like, to cause or direct expression of said antibody upon administration to a subject. Examples of promoters and enhancers used in the expression vector for animal cell include early promoter and enhancer of SV40, LTR promoter and enhancer of Moloney mouse leukemia virus, promoter and enhancer of immunoglobulin H chain and the like. Examples of plasmids include replicating plasmids comprising an origin of replication, or integrative plasmids, such as for instance pUC, pcDNA, pBR, and the like. Examples of viral vector include adenoviral, retroviral, herpes virus and AAV vectors. Such recombinant viruses may be produced by techniques known in the art, such as by transfecting packaging cells or by transient transfection with helper plasmids or viruses.

A further object of the present invention relates to a host cell which has been transfected, infected or transformed by a nucleic acid and/or a vector according to the invention and expressing an antibody according to the invention.

Accordingly such recombinant host cells can be used for the production of antibodies of the invention The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed".

The nucleic acids of the invention may be used to produce an antibody of the invention in a suitable expression system. The term "expression system" means a host cell and compatible vector under suitable conditions, e.g. for the expression of a protein coded for by foreign DNA carried by the vector and introduced to the host cell. Common expression systems include *E. coli* host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli, Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G11.16Ag.20 cell (ATCC CRL1662, hereinafter referred to as "YB2/0 cell"), and the like.

The present invention also relates to a method of producing an antibody according to the invention, said method comprising the steps of: (i) introducing in vitro or ex vivo a recombinant nucleic acid or a vector as described above into a host cell, (ii) culturing in vitro or ex vivo the recombinant host cell obtained at step (i) under suitable conditions for expression of the antibody and (iii), recovering the expressed antibody.

In another particular embodiment, the method comprises the steps of:

(i) culturing an hybridoma under conditions suitable to allow expression of 3327 antibody; and (ii) recovering the expressed antibody from said culture.

Antibodies of the invention are suitably separated from the culture medium by conventional immunoglobulin purification procedures such as, for example, protein G-Sepharose, hydroxyapatite chromatography, gel electrophoresis, dialysis, or affinity chromatography.

In a particular embodiment, a human chimeric antibody of the present invention can be produced by obtaining nucleic sequences encoding VL and VH domains as previously described, constructing a human chimeric antibody expression vector by inserting them into an expression vector for animal cell having genes encoding human antibody CH and human antibody CL, and expressing the coding sequence by introducing the expression vector into an animal cell. As the CH domain of a human chimeric antibody, it may be any region which belongs to human immunoglobulin, but those of IgG class are suitable and any one of subclasses belonging to IgG class, such as IgG1, IgG2, IgG3 and IgG4, can also be used. Also, as the CL of a human chimeric antibody, it may be any region which belongs to Ig, and those of kappa class or lambda class can be used. Methods for producing chimeric antibodies involve conventional recombinant DNA and gene transfection techniques are well known in the art.

A humanized antibody of the present invention may be produced by obtaining nucleic acid sequences encoding CDR domains, as previously described, constructing a humanized antibody expression vector by inserting them into an expression vector for animal cell having genes encoding (i) a heavy chain constant region identical to that of a human antibody and (ii) a light chain constant region identical to that of a human antibody, and expressing the genes by introducing the expression vector into an animal cell.

The humanized antibody expression vector may be either of a type in which a gene encoding an antibody heavy chain and a gene encoding an antibody light chain exists on separate vectors or of a type in which both genes exist on the same vector (tandem type). In respect of easiness of construction of a humanized antibody expression vector, easiness of introduction into animal cells, and balance between the expression levels of antibody H and L chains in animal cells, humanized antibody expression vector of the tandem type is preferred. Methods for producing humanized antibodies based on conventional recombinant DNA and gene transfection techniques are well known in the art. Antibodies can be humanized using a variety of techniques known in the art including, for example, CDR-grafting (EP 239,400; PCT publication WO91/09967; U.S. Pat. Nos. 5,225,539; 5,530,101; and 5,585,089), veneering or resurfacing (EP 592,106; EP 519,596), and chain shuffling (U.S. Pat. No. 5,565,332). The general recombinant DNA technology for preparation of such antibodies is also known (see European Patent Application EP 125023 and International Patent Application WO 96/02576).

The Fab of the present invention can be obtained by treating an antibody which specifically reacts with human HER3 with a protease, papain. Also, the Fab can be produced by inserting DNA encoding Fab of the antibody into a vector for prokaryotic expression system, or for eukaryotic expression system, and introducing the vector into a procaryote or eucaryote (as appropriate) to express the Fab.

The F(ab')2 of the present invention can be obtained treating an antibody which specifically reacts with human HER3 with a protease, pepsin. Also, the F(ab')2 can be produced by binding Fab' described below via a thioether bond or a disulfide bond.

The Fab' of the present invention can be obtained treating F(ab')2 which specifically reacts with human HER3 with a reducing agent, dithiothreitol. Also, the Fab' can be produced by inserting DNA encoding Fab' fragment of the antibody into an expression vector for prokaryote, or an expression vector for eukaryote, and introducing the vector into a prokaryote or eukaryote (as appropriate) to perform its expression.

The scFv of the present invention can be produced by obtaining cDNA encoding the VH and VL domains as previously described, constructing DNA encoding scFv, inserting the DNA into an expression vector for prokaryote, or an expression vector for eukaryote, and then introducing the expression vector into a prokaryote or eukaryote (as appropriate) to express the scFv. To generate a humanized scFv fragment, a well known technology called CDR grafting may be used, which involves selecting the complementary determining regions (CDRs) from a donor scFv fragment, and grafting them onto a human scFv fragment framework of known three dimensional structure (see, e. g., WO98/45322; WO 87/02671; U.S. Pat. Nos. 5,859,205; 5,585,089; 4,816,567; EP0173494).

Amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce of the binding activity. In order to resolve the problem, in antibodies grafted with human CDR, attempts have to be made to identify, among amino acid sequences of the FR of the VH and VL of human antibodies, an amino acid residue which is directly associated with binding to the antibody, or which interacts with an amino acid residue of CDR, or which maintains the three-dimensional structure of the antibody and which is directly associated with binding to the antigen. The reduced antigen binding activity could be increased by replacing the identified amino acids with amino acid residues of the original antibody derived from a non-human animal.

Modifications and changes may be made in the structure of the antibodies of the present invention, and in the DNA sequences encoding them, and still obtain a functional molecule that encodes an antibody with desirable characteristics.

In making the changes in the amino sequences, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

Another type of amino acid modification of the antibody of the invention may be useful for altering the original glycosylation pattern of the antibody. By "altering" is meant deleting one or more carbohydrate moieties found in the antibody, and/or adding one or more glycosylation sites that are not present in the antibody. Glycosylation of antibodies is typically N-linked. "N-linked" refers to the attachment of the carbohydrate moiety to the side chain of an asparagine residue. The tripeptide sequences asparagine-X-serine and asparagines-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites).

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine.

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr H. et al. (1987) and by Edge, A S. et al. (1981). Enzymatic cleavage of carbohydrate moieties on antibodies can be achieved by the use of a variety of endo- and exo-glycosidases as described by Thotakura, N R. et al. (1987).

Another type of covalent modification of the antibody comprises linking the antibody to one of a variety of non proteinaceous polymers, eg., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Immunoconjugates:

An antibody of the invention can be conjugated with a detectable label to form an immunoconjugate. Suitable detectable labels include, for example, a radioisotope, a fluorescent label, a chemiluminescent label, an enzyme label, a bioluminescent label or colloidal gold. Methods of making and detecting such detectably-labeled immunoconjugates are well-known to those of ordinary skill in the art, and are described in more detail below.

The detectable label can be a radioisotope that is detected by autoradiography. Isotopes that are particularly useful for the purpose of the present invention are $^3$H, $^{125}$I, $^{131}$I, $^{35}$S and $^{14}$C.

Immunoconjugates can also be labeled with a fluorescent compound. The presence of a fluorescently-labeled antibody is determined by exposing the immunoconjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine.

Alternatively, immunoconjugates can be detectably labeled by coupling an antibody to a chemiluminescent compound. The presence of the chemiluminescent-tagged immunoconjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label immunoconjugates of the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, immunoconjugates can be detectably labeled by linking a monoclonal antibody to an enzyme. When the enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label polyspecific immunoconjugates include beta-galactosidase, glucose oxidase, peroxidase and alkaline phosphatase.

An antibody of the invention may be labelled with a metallic chemical element such as lanthanides. Lanthanides offer several advantages over other labels in that they are stable isotopes, there are a large number of them available, up to 100 or more distinct labels, they are relatively stable, and they are highly detectable and easily resolved between detection channels when detected using mass spectrometry. Lanthanide labels also offer a wide dynamic range of detection. Lanthanides exhibit high sensitivity, are insensitive to light and time, and are therefore very flexible and robust and can be utilized in numerous different settings. Lanthanides are a series of fifteen metallic chemical elements with atomic numbers 57-71. They are also referred to as rare earth elements. Lanthanides may be detected using CyTOF technology. CyTOF is inductively coupled plasma time-of-flight mass spectrometry (ICP-MS). CyTOF instruments are capable of analyzing up to 1000 cells per second for as many parameters as there are available stable isotope tags.

Those of skill in the art will know of other suitable labels which can be employed in accordance with the present invention. The binding of marker moieties to monoclonal antibodies can be accomplished using standard techniques known to the art.

Moreover, the convenience and versatility of immunochemical detection can be enhanced by using monoclonal antibodies that have been conjugated with avidin, streptavidin, and biotin.

Diagnostic and Therapeutic Methods of the Invention:

Antibodies of the present invention and immunoconjugates can be used for detecting glycoprotein (GP) of Ebola virus, and/or evaluating its amount in a biological sample, in particular a culture medium sample, a whole blood sample, a serum sample, a plasma sample. Therefore they can be used for diagnosing all diseases associated with Ebola Virus.

Accordingly, the method of detection of the invention is consequently useful for the in vitro diagnosis of Ebola Virus Disease.

An object of the invention is a method for detecting glycoprotein (GP) of Ebola virus, and/or evaluating its amount in a biological sample, wherein said method comprises contacting said sample with an antibody or immunoconjugate of the invention under conditions allowing the formation of an immune complex between glycoprotein (GP) of Ebola virus and said antibody/immunoconjugate, and detecting or measuring the immune complex formed.

The immune complex formed can be detected or measured by a variety of methods using standard techniques, including, by way of non-limitative examples, enzyme-linked immunosorbent assay (ELISA) or other solid phase immunoassays, radioimmunoassay, electrophoresis, immunofluorescence, or Western blot.

A further object of the invention is a method for diagnosing Ebola infection, wherein said method comprising evaluating the amount of glycoprotein (GP) of Ebola virus, as indicated above, in a biological sample from a subject to be tested, and comparing with a control value in a normal subject.

As used herein, the term "sample" refers to a biological sample obtained for the purpose of in vitro evaluation. In the methods of the invention, the sample may comprise any body fluid obtained from a subject. In some embodiments, the sample is a bodily fluid such as peripheral blood, cord blood, urine, cerebrospinal fluid, saliva, and lymph. Typical biological samples to be used in the method according to the invention are blood samples (e.g. whole blood sample, serum sample, or plasma sample). A biological sample can be optionally pre-treated or processed prior to be used. Examples of pre-treatment steps include the addition of a reagent such as a stabilizer, a preservative, a fixant, a lysing reagent, a diluent, an anti-apoptotic reagent, a buffering reagent, an osmolarity regulating reagent, a pH regulating reagent, and/or a cross-linking reagent. Thus, a sample, can be analyzed under any of the methods and systems herein within 1 week, 6 days, 5 days, 4 days, 3 days, 2 days, 1 day, 12 hrs, 6 hrs, 3 hrs, 2 hrs, or 1 hr from the time the sample is obtained.

Finally, the invention also provides kits comprising at least one antibody of the invention or a fragment thereof. Kits of the invention can contain an antibody coupled to a solid support, e.g., a tissue culture plate or beads (e.g., sepharose beads). Kits can be provided which contain antibodies for detection and quantification of glycoprotein (GP) of Ebola virus in vitro, e.g. in an ELISA. Such antibody useful for detection may be provided with a label such as a fluorescent or radiolabel.

A further object of the invention relates to an antibody of the invention or a fragment thereof for use as a medicament.

A further object of the invention relates to a pharmaceutical composition comprising an antibody of the invention or a fragment thereof for use in the treatment of Ebola Virus disease.

A further object of the invention relates to a method of treating a Ebola Virus disease comprising administering a subject in need thereof comprising administering the subject with a therapeutically effective amount of an antibody of the invention or a fragment thereof.

As used herein, the term "Ebola virus disease" (EVD), formerly known as Ebola haemorrhagic fever, is a severe, often fatal illness in humans. The incubation period, that is, the time interval from infection with the virus to onset of symptoms is 2 to 21 days. Humans are not infectious until they develop symptoms. First symptoms are the sudden onset of fever fatigue, muscle pain, headache and sore throat. This is followed by vomiting, diarrhoea, rash, symptoms of impaired kidney and liver function, and in some cases, both internal and external bleeding (e.g. oozing from the gums, blood in the stools). Laboratory findings include low white blood cell and platelet counts and elevated liver enzymes.

As used herein, the term "treatment" or "treat" refer to both prophylactic or preventive treatment as well as curative or disease modifying treatment, including treatment of subjects at risk of contracting the disease or suspected to have contracted the disease as well as subjects who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

By a "therapeutically effective amount" of the antibody of the invention is meant a sufficient amount of the antibody to treat Ebola Virus disease, at a reasonable benefit/risk ratio applicable to any medical treatment. It will be understood, however, that the total daily usage of the antibodies and compositions of the present invention will be decided by the attending physician within the scope of sound medical judgment. The specific therapeutically effective dose level for any particular patient will depend upon a variety of factors including the disorder being treated and the severity of the disorder; activity of the specific antibody employed; the specific composition employed, the age, body weight, general health, sex and diet of the patient; the time of administration, route of administration, and rate of excretion of the specific antibody employed; the duration of the treatment; drugs used in combination or coincidental with the specific antibody employed; and like factors well known in the medical arts. For example, it is well known within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

In some embodiments, the antibody of the present invention is used in combination with at least one antiviral compound. In some embodiments, the anti-viral compound is selected from polymerase inhibitors. The second group of polymerase inhibitors which can be used in this type of combination therapy includes, but is not limited to, the compounds having the general formula (I) as defined in the US application with the Ser. No. 61/550,045 filed on Oct. 21, 2011, the compounds having the general formula (II) as defined in U.S. application 61/550,057 filed on Oct. 21, 2011, the compounds disclosed in WO 2011/000566, WO 2010/110231, WO 2010/110409, WO 2006/030807 or U.S. Pat. No. 5,475,109 as well as flutimide and analogues, favipiravir and analogues, epigallocatechin gallate and analogues, as well as nucleoside analogs such as ribavirine.

In other embodiments, the antibody of the invention are used in combination with other neutralizing antibodies, and for example, in combination with one or more antibodies of the MB-003 mAb cocktail (including c13C6, h13F6 and c6D8, Olinger et al 2012, PNAS 109(44): 18030-18035) and/or one or more antibodies of the ZMAb cocktail (including c1H3, c2G4, and c4G7, Qiu et al 2012, Sci Transl Med 4(138): 138ra181).

For administration, the antibody of the invention or the fragment thereof is formulated as a pharmaceutical composition. Accordingly a further object of the invention relates to a pharmaceutical composition comprising an antibody of the invention or a fragment thereof for use in the treatment of Ebola Virus disease. A pharmaceutical composition comprising an antibody of the invention or a fragment thereof can be formulated according to known methods to prepare pharmaceutically useful compositions, whereby the therapeutic molecule is combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Formulations may further include one or more excipients, preservatives, solubilizers, buffering agents, albumin to prevent protein loss on vial surfaces, etc. The form of the pharmaceutical compositions, the route of administration, the dosage and the regimen naturally depend upon the condition to be treated, the severity of the illness, the age, weight, and sex of the patient, etc. The pharmaceutical compositions of the invention can be formulated for a topical, oral, parenteral, intranasal, intravenous, intramuscular, subcutaneous or intraocular. To prepare pharmaceutical compositions, an effective amount of the antibody may be dissolved or dispersed in a pharmaceutically acceptable carrier or aqueous medium. The pharmaceutical forms include sterile aqueous solutions or dispersions; formulations including sesame oil, peanut oil or aqueous propylene glycol; and sterile powders for the extemporaneous preparation of sterile injectable solutions or dispersions. It must be stable under the conditions of manufacture and storage and must be preserved against the contaminating action of microorganisms, such as bacteria and fungi. An antibody of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

The antibodies of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

The invention will be further illustrated by the following figures and examples. However, these examples and figures should not be interpreted in any way as limiting the scope of the present invention.

FIGURES

FIG. 1: Characterization of mAb #3327. (A) Neutralization of EBOV by #3327. EBOV was incubated with the indicated concentrations of #3327 prior to infection. 50% neutralizing titer was determined as the dilution of antibody that neutralizes virus in 50% of the wells as in TCID50 analysis. (B) Cross neutralization assay. VSVΔG-RFP pseudotyped with the indicated filoviral GPs were used to infect Vero E6 cells at MOI 0.5. 8 h post-infection, cells were analysed by flow cytometry for the presence of RFP. Infection % is shown relative to that obtained in the absence of antibody for each virus. (C) and (D) Flow cytometry analysis of VeroE6 cells transfected with pIRES2-eGFP-GP [17]. Detection was performed using #3327 (C) and #3357 (D) and anti-mouse Alexa 555 and GFP.

FIG. 2: MAb #3327 neutralization mechanism. (A) GP region required for staining by #3327. Flow cytometry surface staining of 293T cells expressing GP-WT, $GP_{G528E}$ or GP Δ130-188 using mAbs #3327 and #3373. No staining is observed with $GP_{G528E}$ and GP Δ130-188. (B) Mapping of the internal fusion loop (dark grey) and amino acids 130-188 (light grey surrounded by a black line) on the crystal structure of EBOV GP as defined by Lee et al. [8]. (C) Neutralization assay of VSVΔG-RFP. VSVΔG-RFP pseudotyped with GP-WT, GP G528E, GPΔmucin or GP Q508A were used to infect VeroE6 cells in the presence or absence of 100 μg/ml #3327 as indicated. GPs carrying mutations Q508A or Δmucin are successfully neutralised, whilst mutation G528E is not. Infection % is shown relative to that obtained in the absence of antibody (NT) for each virus. (D) Binding of #3327 to synthetic MBP-HIS-EBOV-GP fusion peptide. A recombinant protein containing fusion peptide was used to evaluate the potential of #3327 to recognize the linear sequence of the fusion peptide by ELISA. No evidence was observed for #3327 binding to the fusion peptide, in contrast to that observed with an anti-HIS antibody used as a positive control.Øindicates absence of coated peptide in wells. (E) Evaluation of the action of mAbs on viral particle binding to cells. RFP-VLPs were allowed to bind to target cells placed on ice in the presence or absence of neutralizing antibodies as indicated. The presence of RFP signal on cells was then measured by flow cytometry. As a control, cells were also treated with trypsin before analysis to evaluate the level of VLP internalization. Results are shown as % fluorescence (MFI) normalised with respect to that obtained with RFP-VLPs in the absence of treatment. (F) Impact of acidification on the interaction between EBOV-GP and #3327. ELISA plates coated with viral particles bearing GP were incubated with #3327 or not (Mock), and then washed with DMEM at pH7, 6, 5.5, 5.0, 4.5 and 2.5, as indicated. Binding is not affected until pH2.5 (G) Neutralization of thermolysin-digested-VSV-GP particles by #3327. Recombinant VSV-EBOV-GP particles were either thermolysin- (ThLy) or mock-treated (NT) and then subjected to neutralization by 100 μg/ml #3327 as indicated. After 1 hour, samples were titrated by plaque assay. (H) GP binding to NPC1 in the presence of #3327. Mock treated or thermolysin digested recombinant VSV-EBOV-GP particles were coated on polysorb plates overnight as indicated and then incubated with soluble, HIS-tagged, NPC1 loop C construct (4) with or without mAbs at 100 μg/ml. The presence of NPC1 was detected using an anti-HIS HRP. *p=0.022 in a student t test.

EXAMPLE

Screening assays for functional properties of antibodies of the invention

1. Binding to a Conformational Epitope of GP EBOV

10e6 VSV GP recombinant viruses (5) per well (in 50 μl) are coated overnight in a polysorb Elisa plate, then a blocking step is performed with 200 μl of PBS 5% skimmed milk for 2 hrs at 4°. Mab 3327 is then added at 0.1 mg/ml in 1% milk PBS for 1 hr at 4°. Detection is performed by addition of an anti mouse HRP secondary antibody (1/2000 Dako) for one hour at 4° and subsequent addition of 50 μl TMB substrate. Each steps include removal of the previous solution and 3 washes with 200 μl of PBS.

2. Binding to Thermolysin Digested Form of Ebolavirus Glycoprotein GP

Binding assay can be performed substantially the same way as described in previous section except that thermolysin digested form of EBOV GP is used.

Thermolysin digestion is performed accordingly to the protocol described by Chandran et al (11). Briefly 20 μg of purified VSV GP (5) are incubated with 0.5 mg/ml thermolysin (Promega) in 50 mM tris ph8,8, 0.5 mM CaCl2 during 40 minutes at 37°. Digestion is stopped by addition of EDTA (0.1M final concentration). Digestion efficiency can be measured by visualisation of mature GP1 disappearance.

Seroneutralization Assay

Seroneutralization is performed as a typical SN50 assay using 200TCID50 of Ebola GFP as inoculum. Five time successive dilutions of antibody are incubated with 200TCID50 in 0.1 ml of DMEM for 30 minutes then placed onto vero cells in quadruplicate. After one hour, 5% FCS DMEM is added and cells are incubated for 6 days prior revelation by cristal violet. SN50 is determined as the dilution of antibody that neutralize virus in 50% of the wells.

3. Prevention of Translocation of Genetic Material of Ebolavirus to the Cytosol of Infected Cells This property can be indirectly confirmed by the following assays:

Increase Affinity of Digested GP Binding to NPC Receptor Upon Binding of the Antibody 10e6 thermolysin digested VSV GP recombinant viruses per well (in 50 μl) are coated overnight in a polysorb Elisa plate, then a blocking step is performed with 200 μl of PBS 5% skimmed milk for 2 hrs at 4°. Mab 3327 is then added at 0.1 mg/ml in 1% milk PBS for 1 hr at 4° together with 50 μg soluble NPC1 (containing an His tag). Detection is performed by addition of an anti mouse His tag HRP secondary antibody (1/2000 Miltenyi) for one hour at 4° and subsequent addition of 50 μl TMB substrate. Each steps include removal of the previous solution and 3 washes with 200 μl of PBS.

Material & Methods of Experimental Part

Viruses and Cell Lines

Recombinant Ebolavirus Zaire, strain Mayinga, was generated as described earlier [15] and used for infection of HEK 293T and Vero E6 cells cultured at 37° C. in Dulbecco's modified Eagle's medium (Invitrogen) supplemented with 10% fetal calf serum (FCS). Experiments using Ebola virus were performed in the BSL4 INSERM laboratory Jean Merieux (Lyon, France). Recombinant VSV virus encoding EBOV-GP was created earlier and described in [16]. The virus was routinely grown in Vero E6 cells as above.

Hybridoma Generation and Culture

Generation of hybridomas was performed as described previously [14]. Hybridomas were grown in DMEM/F12 10% FCS containing Glutamine and adapted to Protein Free Hybridoma medium (Invitrogen®) for growth in Integra Celline® high density culture flasks. MAb #3327 is an IgG1k as determined by Mouse Isotyping strips (Santa Cruz).

Plasmid Construction

Mutagenesis to insert mutation G528E into phCMV-GP plasmid [17] was performed using the Stratagene Quik change site-directed mutagenesis kit. Plasmid phCMV-GPΔ130-188 was generated by overlapping extension PCR with flanking primers to the 5" and 3" ends of cDNA for EBOV-GP as well as complementary internal primers flanking the deleted sequence.

Transfection of Cells.

HEK 293T or VeroE6 cells were grown to 60% confluence, before transfection with Exgen500 reagent (Euromedex) according to manufacturer's instructions. After 6 h of incubation at 37° C., DMEM supplemented with 10% FCS was added to the cells. Analysis of expression was performed at the time points indicated.

Immunofluorescence and Flow Cytometry

Cells were transfected as described above with the indicated plasmids. For flow cytometry, cells were stained with monoclonal antibody #3327 and secondary donkey anti-mouse Alexa 555 antibody (Invitrogen) or analysed for the presence of RFP. A Gallios (Beckman coulter) and a LSR II (Becton Dickinson) flow cytometer were used.

Recombinant Protein Production

The recombinant construct encoding the synthetic EBOV GP fusion peptide fused to MBP was cloned into pMal C2g (neb): MBP-GGS-HHHHHH-GGS-QDEGAAIGLAWIPY-FGPAAE (SED ID N:17). Prokaryotic expression was performed in Rosetta 2 *E. coli* bacteria and protein was purified from bacterial lysate with Cobalt resin (Pierce).

Generation of Pseudotyped VSVΔG-RFP Particles

To produce pseudotyped VSVΔG-RFP particles, first the full length plasmid of VSV-EBOV GP (ref) was digested by Nhe/XhoI (New England Biolabs) to replace the EBOV-GP open reading frame with that of red fluorescent protein (RFP). Virus recovery was performed as in [16] with VSV-G expressed in trans. For pseudotyping, HEK293T cells were transfected with relevant plasmids encoding glycoproteins representing the different filoviruses as indicated, and 24 hours later cells were infected at MOI 0.5 with VSVΔG-

RFP-transG. One day later, supernatants were harvested, cleared from cell debris by low-speed centrifugation and viral particles were pelleted at 250,000 g for 2 h. Virus stocks were titrated using a tissue culture inducing fluorescence 50 (TCIF50) titration assay based upon a classical TCID50 method.

Neutralization Assay

Virus neutralization was performed using 200 TCID50 of EBOV as inoculum. Fivefold successive dilutions of antibody were incubated with virus in 0.1 ml of DMEM for 30 minutes then placed onto Vero E6 cells in quadruplicate. After one hour, 5% FCS DMEM was added and cells were incubated for 6 days prior to revelation by crystal violet. 50% neutralising titer was determined as the dilution of antibody that neutralizes virus in 50% of the observed wells Generation of Escape Mutants Vero E6 cells were infected at MOI 1 with EBOV pre-treated for 1 h at 37° with 5 µg/ml of #3327. Post-infection, cells were incubated for 3 days in DMEM 3% FCS containing 5 µg/ml #3327. After 3 days, supernatant was harvested, diluted at 1:100, and used to infect fresh cells in the presence of #3327 as above. After 4 consecutive passages, viruses were cloned by limiting dilution before analysis and sequencing.

Resistance of the GP-#3327 Complex to Acidification

VSVΔG-RFP-GP particles (2.106 TCIF50/well) were coated on polysorb ELISA plates (Nunc) before saturation with PBS containing 5% skimmed milk for 30 minutes at 4° C. MAb #3327 was added at 100 µg/ml to wells for 1 hour at 4° C. Wells were then incubated with DMEM ranging from pH7 to pH2.5 as indicated, for 10 minutes at room temperature before two washing steps to remove unbound antibody. After washing, secondary anti-mouse HRP antibody (Dako) was then added and detection was performed using TMB substrate.

Thermolysin Digestion

Thermolysin digestion was performed according to the protocol described by Chandran et al [18]. Briefly, 20 µg of purified VSV-GP (measured as total protein) [16] were incubated with 0.5 mg/ml thermolysin (Promega) in 50 mM TRIS pH8,8, 0.5 mM CaCl2 for 40 minutes at 37° C. Digestion was stopped by the addition of EDTA (0.1M final concentration). Digestion efficiency was measured by Western blot analysis.

Results

The neutralization capacity of mAb #3327 was first investigated by classical neutralization assay. Briefly, Vero E6 cells were seeded in 96 well plates 24 h before infection with 200 TCID50 of Ebolavirus as inoculum in the presence of decreasing concentrations of #3327 as indicated (FIG. 1A) and infection was monitored for 6 days post-inoculation. As illustrated in FIG. 1A, #3327 was shown to display a 50% neutralisation titer of 4 µg/ml. Next we investigated the ability of this mAb to show cross-species neutralization using VSVΔG-RFP pseudotyped with different filoviral glycoproteins, as indicated (FIG. 1B). As well as confirming the efficient neutralizing activity of #3327 against EBOV, results also demonstrate a significant cross-species neutralizing activity against ebolavirus Reston (REBOV) and Tai Forest (TEBOV) glycoproteins. Little neutralizing activity was seen against ebolavirus bundibugyo (BEBOV) or Marburg virus (MARV), whilst no affect was seen for Lloviu virus.

It is interesting to note that #3327 is able to stain the surface of cells expressing EBOV GP (FIG. 1C), but proved incapable to interact with GP with Western blot analysis suggesting that this antibody recognizes a conformational epitope. When GP-expressing cells were analysed by flow cytometry it appears that #3327 is likely to target an epitope that is not present on the upper part of the viral spike but rather one that is shielded when GP is expressed at a high concentration on the cell surface. This shielding therefore leads to a decrease in the number of double stained cells and the classic "tailing off" profile of cells that are found positive for surface GP, as GP expression increases [14]. Indeed, as shown in FIG. 1C, this characteristic shielding phenotype is seen with flow cytometry when cells are analysed using both #3327 staining and GFP (expressed in tandem with GP gene using an internal IRES sequence). This is certainly evident when the profile is contrasted with that of mAb #3357, another mAb that was identified previously [14], and that gives a flow cytometry phenotype that clearly indicates a correlation between GP and GFP expression and recognition by the antibody targeting the GP spike (FIG. 1D). Such a profile indicates that the Mab is targeting an epitope present on the upper or outer surface of GP and is therefore not shielded from recognition even with a high expression level of surface GP. In agreement with the profile obtained above for #3327, its ability to recognize a GP mutant that no longer contains its mucin domain again supports the notion that it is likely to recognize an epitope located in the lower part of the viral GP spike (FIG. 2C).

To identify the GP epitope recognized by #3327, we performed a selection of escape mutants by growing Ebolavirus for several consecutive passages in the presence of #3327 (5 µg/ml). After 4 passages and a cloning step using a limiting dilution procedure, eight individual clones were selected and propagated in the presence of antibody before analysis for the presence of mutations in the GP gene. All selected variants that escaped from neutralization displayed a single glycine to glutamic acid amino acid (aa) change at position 528, present in the internal fusion loop of GP.

Next, the importance of this aa substitution for the ability of the virus to escape neutralization was confirmed by the absence of staining with #3327 for cells transiently expressing GP-G528E (FIG. 2A). As control, cells expressing either GP-WT or GP-G528E were found to be stained with another mAb. Interestingly, #3327 was also incapable of recognising the GP deletion mutant (GPΔ130-188) lacking amino acids 130-188 known to be part of the putative receptor binding domain [19]. Identification of the region involved in recognition of GP by #3327 was further confirmed in experiments with pseudotyped-VSV particles expressing RFP from a separate transcription cassette and bearing GP-G528E (FIG. 2C). In these experiments, #3327 was shown to be incapable of neutralizing such particles as measured by flow cytometry using RFP (FIG. 2C). On the contrary, particles bearing GP-WT were again effectively neutralized by #3327.

Previously a mutation in the glutamine at position 508 of GP was shown to impair binding of several neutralizing antibodies including KZ52, c2G4 and c2G7 [20]. It is interesting to note that pseudotyped-VSV particles bearing this mutation were efficiently neutralized by #3327 (FIG. 2C), indicating an important difference between these previously characterized neutralizing antibodies and #3327.

In an attempt to more precisely identify the binding epitope of #3327, we produced and assayed a chimeric protein consisting of the sequence coding for the EBOV-GP fusion peptide fused with the maltose binding protein and separated by a 6×His tag (MBP-HIS-EBOV-GP). This protein, when expressed in bacterial cells, did interact with antibodies against the 6×His tag in ELISA but not with #3327, in agreement with the fact that #3327 did not recognize denatured GP in Western Blot analysis and is thus likely to recognize a conformational structure.

Recently a 3D structure of EBOV GP had been presented by Lee et al [8]. When the internal fusion loop was mapped onto the GP structure (FIG. 2B, shown in dark grey) it was found to locate to a region in spatial proximity with part of the putative receptor binding domain (RDB) (130-188 aa, shown in light grey) [8, 19]. The data presented so far for the EBOV escape mutants and an absence of interaction between #3327 and GP-G528E or between #3327 and GPΔ130-188 are consistent with the idea that the epitope for #3327 might cover both these regions and that mutation G528E results in a conformational change that prevents interaction of the antibody with mutated GP. In this regard, such a binding epitope is likely to be located on the side of the chalice-like structure made by the trimeric GP complex and this is also in agreement with our findings that the #3327 epitope is shielded when GP is overexpressed in cells. Interestingly KZ52, a neutralizing antibody obtained from a survivor of EBOV infection displays a somewhat similar phenotype in flow cytometry [8, 21].

As stated above, Ebolavirus entry is a complex, multistep process. Understanding the mechanism of Ebolavirus neutralization by antibodies is thus of general interest and also is important for success in fighting infection and for the development of future therapeutic strategies. In order to understand further the molecular details of #3327 neutralization of EBOV infection we next investigated whether #3327 affects the binding of virions to the cell surface. In this case we used VLPs produced upon co-expression of EBOV GPs and matrix protein VP40 fused with RFP in 293T cells, as described in [22]. As seen in FIG. 3B, the presence of #3327 does not significantly affect binding of fluorescent VLPs to cells incubated on ice. Treatment of cells with trypsin for 5 min at 37° C. reduced the amount of surface bound VLPs, allowing us to evaluate the level of internalization of VLPs in this assay. As expected, a non-relevant (NR) antibody targeting GP used as a further control, also failed to inhibit binding of VLPs to cells (FIG. 2E). This data suggest that #3327 is likely neutralizing virus infection after internalization into endosomes but before actual membrane fusion. In order to verify whether #3327 is able to maintain its association with GP during the endosomal/lysosomal steps of viral entry we investigated the stability of GP-#3327 complexes after treatment at different pH, ranging from 2.5-7.6 using ELISA, as indicated (FIG. 2F). As demonstrated, moderate acid pH treatment does not lead to dissociation of the antibody/GP complex, suggesting that such an interaction would be maintained within the cellular endolysosomal compartment.

Next, to investigate whether #3327 is still able to neutralize the proteolytically cleaved form of viral GP we digested VSV-GP virions with thermolysin to mimic the action of cellular cathepsins. This digestion results in the disappearance of a large part of the GP1 subunit and in an increase in virus titer, as previously described [23]. As shown, #3327 is able to recognize and neutralize Ebola GP both in its natural form and also in a thermolysin-digested form, as 50 μg/ml of #3327 was able to fully neutralize both digested and non-digested VSV GP (FIG. 2G). To test this idea further and to identify if #3327 interferes in the interaction between GP and intracellular receptor NPC1, we performed a binding assay using a soluble NPC1 loop C protein provided by K. Chandran. With this binding assay, and as described in the literature, we confirm that only the digested form of GP can bind to NPC1 (FIG. 2H). Interestingly, we show that #3327 does not block the association of digested GP with the NPC1 loop C. More notably, the experiment shows that there is a slight increase in binding between NPC1 and thermolysin treated GP in the presence of #3327. It is interesting to speculate that this increase in NPC1 binding is due to the ability of #3327 to stabilize the digested GP structure through binding to both the RBD, within GP1, and GP2. This stabilization may therefore prevent the conformational shift between pre-fusion state and fusion-competent state occurring after NPC1 binding. Mechanisms of neutralization involving a blocking of the conformational change required for membrane fusion have previously been suggested for a number of other neutralizing antibodies, including KZ52, c2g4, c4g7 and 16F6 (12). Structural studies would suggest that these antibodies are targeting regions of the GP spike where they can prevent the series of structural rearrangements that are required for the viral fusion process. Our data confirms that this step is likely highly critical for viral entry into a target cell. In a somewhat related mechanism we believe that binding of #3327 to viral GP is reinforcing the interaction with NPC1 and thus preventing the degree of flexibility needed by GP to achieve its final fusion-competent conformation. The #3327 mAb presented here is targeting a different GP2 epitope than those that were described previously and importantly this antibody is still able to block entry of viruses displaying the Q508 mutation that often allows viral escape from neutralisation with antibodies.

In conclusion this study describes a novel monoclonal antibody displaying unique properties and offers insights for future development of antibody-based treatments. Importantly, the treatment with a cocktail of antibodies including #3327 would help to avoid the appearance of resistant variants like for example the Q508 escape mutant that had been associated with lethality in antibody-treated monkeys.

TABLE 3

Brief description of useful amino acid and nucleotide sequences for practicing the invention

| SEQ ID NO: | Brief description of the sequences |
|---|---|
| 1 | Nucleotide sequence of VH domain of mAb 3327 (Kabat definition) |
| 2 | Nucleotide sequence of HCDR1 of mAb 3327 (Kabat definition) |
| 3 | Nucleotide sequence of HCDR2 of mAb 3327 (Kabat definition) |
| 4 | Nucleotide sequence of HCDR3 of mAb 3327 (Kabat definition) |
| 5 | Amino acid sequence of VH domain of mAb 3327 (Kabat definition) |
| 6 | Amino acid sequence of HCDR1 of mAb 3327 (Kabat definition) |
| 7 | Amino acid sequence of HCDR2 of mAb 3327 (Kabat definition) |
| 8 | Amino acid sequence of HCDR3 of mAb 3327 (Kabat definition) |
| 9 | Nucleotide sequence of VL domain of mAb 3327 (Kabat definition) |
| 10 | Nucleotide sequence of LCDR1 of mAb 3327 (Kabat definition) |
| 11 | Nucleotide sequence of LCDR2 of mAb 3327 (Kabat definition) |
| 12 | Nucleotide sequence of LCDR3 of mAb 3327 (Kabat definition) |
| 13 | Amino acid sequence of VL domain of mAb 3327 (Kabat definition) |
| 14 | Amino acid sequence of LCDR1 of mAb 3327 (Kabat definition) |
| 15 | Amino acid sequence of LCDR2 of mAb 3327 (Kabat definition) |
| 16 | Amino acid sequence of LCDR3 of mAb 3327 (Kabat definition) |
| 17 | Amino acid sequence of peptide fused to MBP |
| 18 | Native amino acid sequence of Ebolavirus subunit GP |

TABLE 4

Useful amino acid and nucleotide sequences for practicing the invention

| SEQ ID NO: | Corresponding amino acid or nucleotide sequences |
|---|---|
| 1 | GAGGTGCAGCTTCAGGAGTCAGGACCTAGCCTCGGGAAACCTTCTCAG<br>ACTCTGTCCCTCACCTGTTCTGTCACTGGCGACTCCATCACCAGTGGTT<br>ACTGGAACTGGATCCGGAAATTCCCAGGGAGTAAGCTTGAGTACATGG<br>GGTACATAACCTCCAGTGGTAGCACTTACTACAATCCATCTCTCAAAA<br>GTCGCATCTCCATCACTCGAGACACATCCAAGAACCAGTATTACCTGC<br>AGTTGAATTCTGTGACTTCTGAGGACACAGCCACCTATTACTGTGCAA<br>GAGAAGGGGCCCGATCATCCGGGGGCTGGTACTTCGATGTCTGGGGCG<br>CAGGGACCACGGTCACCGTCTCCTCA |
| 2 | GGCGACTCCATCACCAGTGGTTACTGGAAC |
| 3 | TACATAACCTCCAGTGGTAGCACTTACTACAATCCATCTCTCAAAAGT |
| 4 | GAAGGGGCCCGATCATCCGGGGGCTGGTACTTCGATGTC |
| 5 | EVQLQESGPSLGKPSQTLSLTCSVTGDSITSGYWNWIRKFPGSKLEYMGYI<br>TSSGSTYYNPSLKSRISITRDTSKNQYYLQLNSVTSEDTATYYCAREGARSS<br>GGWYFDVWGAGTTVTVSS |
| 6 | GDSITSGYWN |
| 7 | YITSSGSTYYNPSLKS |
| 8 | EGARSSGGWYFDV |
| 9 | GACATTGTGATGACCCAGTCTCACAAATTCATGTCCACATCAGTAGGA<br>GACAGGGTCAGCATCACCTGCAAGGCCAGTCAGGATGTGAGTTCTGCT<br>GTAGTTTGGTATCAACAAAAACCAGGGCAATCTCCTAAACTACTGATT<br>TACTGGGCATCCACCCGGCACACTGGAGTCCCTGATCGCTTCACAGGC<br>AGTGGATCTGGGACAGATTATACTCTCACCATCAGCAGTGTGCAGGCT<br>GAAGACCTGGCACTTTATTACTGTCAGCAACATTATAGCACTCCGACG<br>TTCGGTGGAGGCACCAAGCTGGAAATCAAACGGGCT |
| 10 | AAGGCCAGTCAGGATGTGAGTTCTGCTGTAGTT |
| 11 | TGGGCATCCACCCGGCACACT |
| 12 | CAGCAACATTATAGCACTCCGACG |
| 13 | DIVMTQSHKFMSTSVGDRVSITCKASQDVSSAVVWYQQKPGQSPKLLIY<br>WASTRHTGVPDRFTGSGSGTDYTLTISSVQAEDLALYYCQQHYSTPTFGG<br>GTKLEIKRA |
| 14 | KASQDVSSAVV |
| 15 | WASTRHT |
| 16 | QQHYSTPT |
| 17 | GGS-HHHHHH-GGS-QDEGAAIGLAWIPYFGPAAE |
| 18 | MGVTGILQLP RDRFKRTSFF LWVIILFQRT FSIPLGVIHN STLQVSDVDK<br>LVCRDKLSST NQLRSVGLNL EGNGVATDVP SATKRWGFRS<br>GVPPKVVNYE AGEWAENCYN LEIKKPDGSE CLPAAPDGIR<br>GFPRCRYVHK VSGTGPCAGD FAFHKEGAFF LYDRLASTVI<br>YRGTTFAEGV VAFLILPQAK KDFFSSHPLR EPVNATEDPS SGYYSTTIRY<br>QATGFGTNET EYLFEVDNLT YVQLESRFTP QFLLQLNETI YTSGKRSNTT<br>GKLIWKVNPE IDTTIGEWAF WETKKNLTRK IRSEELSFTV VSNGAKNISG<br>QSPARTSSDP GTNTTTEDHK IMASENSSAM VQVHSQGREA<br>AVSHLTTLAT ISTSPQSLTT KPGPDNSTHN TPVYKLDISE ATQVEQHHRR<br>TDNDSTASDT PSATTAAGPP KAENTNTSKS TDFLDPATTT<br>SPQNHSETAG NNNTHHQDTG EESASSGKLG LITNTIAGVA<br>GLITGGRRTR REAIVNAQPK CNPNLHYWTT QDEGAAIGLA<br>WIPYFGPAAE GIYIEGLMHN QDGLICGLRQ LANETTQALQ<br>LFLRATTELR TFSILNRKAI DFLLQRWGGT CHILGPDCCI EPHDWTKNIT<br>DKIDQIIHDF VDKTLPDQGD NDNWWTGWRQ WIPAGIGVTG<br>VIIAVIALFC ICKFVF |

REFERENCES

Throughout this application, various references describe the state of the art to which this invention pertains.

1. Feldmann H, Geisbert T W. Ebola haemorrhagic fever. Lancet 2011; 377:849-62.
2. Ito H, Watanabe S, Takada A, Kawaoka Y. Ebola virus glycoprotein: proteolytic processing, acylation, cell tropism, and detection of neutralizing antibodies. J Virol 2001; 75:1576-80.
3. Chan S Y, Speck R F, Ma M C, Goldsmith M A. Distinct mechanisms of entry by envelope glycoproteins of Marburg and Ebola (Zaire) viruses. J Virol 2000; 74:4933-7.
4. Yang Z, Delgado R, Xu L, et al. Distinct cellular interactions of secreted and transmembrane Ebola virus glycoproteins. Science 1998; 279:1034-7.
5. Mulherkar N, Raaben M, de la Torre J C, Whelan S P, Chandran K. The Ebola virus glycoprotein mediates entry via a non-classical dynamin-dependent macropinocytic pathway. Virology 2011; 419:72-83.
6. Chandran K, Sullivan N J, Felbor U, Whelan S P, Cunningham J M. Endosomal proteolysis of the Ebola virus glycoprotein is necessary for infection. Science 2005; 308: 1643-5.
7. Carette J E, Raaben M, Wong A C, et al. Ebola virus entry requires the cholesterol transporter Niemann-Pick C1. Nature 2011; 477:340-3.
8. Lee J E, Fusco M L, Hessell A J, Oswald W B, Burton D R, Saphire E O. Structure of the Ebola virus glycoprotein bound to an antibody from a human survivor. Nature 2008; 454:177-82.
9. Shedlock D J, Bailey M A, Popernack P M, Cunningham J M, Burton D R, Sullivan N J. Antibody-mediated neutralization of Ebola virus can occur by two distinct mechanisms.

Virology 2010; 401:228-35.

10. Qiu X, Audet J, Wong G, et al. Sustained protection against Ebola virus infection following treatment of infected nonhuman primates with ZMAb. Scientific reports 2013; 3:3365.
11. Oswald W B, Geisbert T W, Davis K J, et al. Neutralizing antibody fails to impact the course of Ebola virus infection in monkeys. PLoS Pathog 2007; 3:e9.
12. Gupta M, Mahanty S, Bray M, Ahmed R, Rollin P E. Passive transfer of antibodies protects immunocompetent and immunodeficient mice against lethal Ebola virus infection without complete inhibition of viral replication. J Viol 2001; 75:4649-54.
13. Reynard O, Volchkov V, Peyrefitte C. [A first outbreak of Ebola virus in West Africa]. Med Sci (Paris) 2014; 30:671-3.
14. Reynard O, Borowiak M, Volchkova V A, Delpeut S, Mateo M, Volchkov V E. Ebolavirus glycoprotein G P masks both its own epitopes and the presence of cellular surface proteins. J Viol 2009; 83:9596-601.
15. Volchkov V E, Volchkova V A, Muhlberger E, et al. Recovery of infectious Ebola virus from complementary DNA: RNA editing of the G P gene and viral cytotoxicity. Science 2001; 291:1965-9.
16. Garbutt M, Liebscher R, Wahl-Jensen V, et al. Properties of replication-competent vesicular stomatitis virus vectors expressing glycoproteins of filoviruses and arenaviruses. J Virol 2004; 78:5458-65.
17. Alazard-Dany N, Volchkova V, Reynard O, et al. Ebola virus glycoprotein G P is not cytotoxic when expressed constitutively at a moderate level. J Gen Virol 2006; 87:1247-57.
18. Miller E H, Obernosterer G, Raaben M, et al. Ebola virus entry requires the host-programmed recognition of an intracellular receptor. EMBO J 2012; 31:1947-60.
19. Kuhn J H, Radoshitzky S R, Guth A C, et al. Conserved receptor-binding domains of Lake Victoria marburgvirus and Zaire ebolavirus bind a common receptor. J Biol Chem 2006; 281:15951-8.
20. Murin C D, Fusco M L, Bornholdt Z A, et al. Structures of protective antibodies reveal sites of vulnerability on Ebola virus. Proc Natl Acad Sci USA 2014.
21. Maruyama T, Parren P W, Sanchez A, et al. Recombinant human monoclonal antibodies to Ebola virus. J Infect Dis 1999; 179 Suppl 1:S235-9.
22. Schudt G, Kolesnikova L, Dolnik O, Sodeik B, Becker S. Live-cell imaging of Marburg virus-infected cells uncovers actin-dependent transport of nucleocapsids over long distances. Proc Natl Acad Sci USA 2013; 110:14402-7.
23. Schomberg K, Matsuyama S, Kabsch K, Delos S, Bouton A, White J. Role of endosomal cathepsins in entry mediated by the Ebola virus glycoprotein. J Virol 2006; 80:4174-8

The invention claimed is:

1. An isolated neutralizing antibody characterized in that it binds to a conformational epitope of Ebolavirus glycoprotein GP of SEQ ID NO:18, wherein said antibody has an SN50 of 10 μg/ml or below as measured in a seroneutralization assay with Zaire Ebolavirus, and is selected from the group consisting of:
   (i) an antibody comprising a heavy chain having the a VH-CDR1 as set forth in SEQ ID NO:6, VH-CDR2 as set forth in SEQ ID NO:7 and VH-CDR3 as set forth in SEQ ID NO:8 and a light chain having the a VL-CDR1 as set forth in SEQ ID NO:14, VL-CDR2 as set forth in SEQ ID NO:15 and VL-CDR3 as set forth in SEQ ID NO:16;
   (ii) a murine antibody which comprises the a VL domain of SEQ ID NO:5 and the a VH domain of SEQ ID NO:13;
   (iii) a chimeric or humanized antibody obtained from the murine antibody of ii); and,
   (iv) the antigen-binding fragments of any of the antibodies an antibody of i) to iii).

2. The isolated neutralizing antibody of claim 1, wherein said isolated neutralizing antibody has at least one of more the following properties:
   (i) it binds to a thermolysin digested form of Ebolavirus glycoprotein GP;
   (ii) it further neutralizes Sudan, Reston and TaïForrest Ebolavirus species;
   (iii) it does not bind to a mutant EBOV GP having a G528E amino acid mutation; and/or,
   (iv) it neutralizes a mutant strain of Ebolavirus having GP with escape mutation Q508A.

3. The isolated neutralizing antibody of claim 1, wherein said isolated neutralizing antibody prevents translocation of genetic material of Ebolavirus in the cytosol.

4. The isolated neutralizing antibody of claim 1, wherein said antigen-binding fragments are selected from Fv, Fab, F(ab')2, Fab', dsFv, scFv, sc(Fv)2, diabodies, tribodies and tetrabodies.

5. The isolated neutralizing antibody of claim 1, which comprises a VL domain having at least 70% identity to SEQ ID NO:13 and a VH domain having at least 70% identity to SEQ ID NO:5.

6. A nucleic acid encoding the light chain and/or the heavy chain of the antibody according to claim 1.

7. A vector comprising the nucleic acid of claim 6.

8. A host cell comprising the nucleic acid of claim 6 or a vector comprising the nucleic acid wherein the host cell is capable of expressing the antibody encoded by the nucleic acid.

9. A pharmaceutical composition comprising the antibody according to claim 1 and at least one pharmaceutically acceptable excipient.

\* \* \* \* \*

SEQUENCE LISTING

```
<160> NUMBER OF SEQ ID NOS: 18

<210> SEQ ID NO 1
<211> LENGTH: 363
<212> TYPE: DNA
<213> ORGANISM: Artificial
<220> FEATURE:
<223> OTHER INFORMATION: Synthetic Nucleotide sequence of VH domain of
      mAb 3327

<400> SEQUENCE: 1
gaggtgcagc ttcaggagtc aggacctagc ctcgggaaac cttctcagac tctgtccctc      60
acctgttctg tcactggcga ctccatcacc agtggttact ggaactggat ccggaaattc     120
ccagggagta agcttgagta catgggtac ataacctcca gtggtagcac ttactacaat      180
ccatctctca aaagtcgcat ctccatcact cgagacacat ccaagaacca gtattacctg     240
cagttgaatt ctgtgacttc tgaggacaca gccacctatt actgtgcaag agaaggggcc     300
```

```
cgatcatccg ggggctggta cttcgatgtc tggggcgcag ggaccacggt caccgtctcc      360
tca                                                                    363
```

<210> SEQ ID NO 2
<211> LENGTH: 30
<212> TYPE: DNA
<213> ORGANISM: Artificial
<220> FEATURE:
<223> OTHER INFORMATION: Synthetic Nucleotide sequence of HCDR1 of mAb
      3327

<400> SEQUENCE: 2

```
ggcgactcca tcaccagtgg ttactggaac                                        30
```

<210> SEQ ID NO 3
<211> LENGTH: 48
<212> TYPE: DNA
<213> ORGANISM: Artificial
<220> FEATURE:
<223> OTHER INFORMATION: Synthetic Nucleotide sequence of HCDR2 of mAb
      3327

<400> SEQUENCE: 3

```
tacataacct ccagtggtag cacttactac aatccatctc tcaaaagt                    48
```

<210> SEQ ID NO 4
<211> LENGTH: 39
<212> TYPE: DNA
<213> ORGANISM: Artificial
<220> FEATURE:
<223> OTHER INFORMATION: Synthetic Nucleotide sequence of HCDR3 of mAb
      3327

<400> SEQUENCE: 4

```
gaaggggccc gatcatccgg gggctggtac ttcgatgtc                              39
```

<210> SEQ ID NO 5
<211> LENGTH: 121
<212> TYPE: PRT
<213> ORGANISM: Artificial
<220> FEATURE:
<223> OTHER INFORMATION: Synthetic Amino acid sequence of VH domain of
      mAb 3327

<400> SEQUENCE: 5

```
Glu Val Gln Leu Gln Glu Ser Gly Pro Ser Leu Gly Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Phe Pro Gly Ser Lys Leu Glu Tyr Met
        35                  40                  45

Gly Tyr Ile Thr Ser Ser Gly Ser Thr Tyr Tyr Asn Pro Ser Leu Lys
    50                  55                  60

Ser Arg Ile Ser Ile Thr Arg Asp Thr Ser Lys Asn Gln Tyr Tyr Leu
65                  70                  75                  80

Gln Leu Asn Ser Val Thr Ser Glu Asp Thr Ala Thr Tyr Tyr Cys Ala
                85                  90                  95

Arg Glu Gly Ala Arg Ser Ser Gly Gly Trp Tyr Phe Asp Val Trp Gly
            100                 105                 110

Ala Gly Thr Thr Val Thr Val Ser Ser
        115                 120
```

```
<210> SEQ ID NO 6
<211> LENGTH: 10
<212> TYPE: PRT
<213> ORGANISM: Artificial
<220> FEATURE:
<223> OTHER INFORMATION: Synthetic Amino acid sequence of HCDR1 of mAb
      3327

<400> SEQUENCE: 6

Gly Asp Ser Ile Thr Ser Gly Tyr Trp Asn
1               5                   10

<210> SEQ ID NO 7
<211> LENGTH: 16
<212> TYPE: PRT
<213> ORGANISM: Artificial
<220> FEATURE:
<223> OTHER INFORMATION: Synthetic Amino acid sequence of HCDR2 of mAb
      3327

<400> SEQUENCE: 7

Tyr Ile Thr Ser Ser Gly Ser Thr Tyr Tyr Asn Pro Ser Leu Lys Ser
1               5                   10                  15

<210> SEQ ID NO 8
<211> LENGTH: 13
<212> TYPE: PRT
<213> ORGANISM: Artificial
<220> FEATURE:
<223> OTHER INFORMATION: Synthetic Amino acid sequence of HCDR3 of mAb
      3327

<400> SEQUENCE: 8

Glu Gly Ala Arg Ser Ser Gly Gly Trp Tyr Phe Asp Val
1               5                   10

<210> SEQ ID NO 9
<211> LENGTH: 324
<212> TYPE: DNA
<213> ORGANISM: Artificial
<220> FEATURE:
<223> OTHER INFORMATION: Synthetic Nucleotide sequence of VL domain of
      mAb 3327

<400> SEQUENCE: 9
gacattgtga tgacccagtc tcacaaattc atgtccacat cagtaggaga cagggtcagc      60
atcacctgca aggccagtca ggatgtgagt tctgctgtag tttggtatca acaaaaacca     120
gggcaatctc ctaaactact gatttactgg gcatccaccc ggcacactgg agtccctgat     180
cgcttcacag gcagtggatc tgggacagat tatactctca ccatcagcag tgtgcaggct     240
gaagacctgg cactttatta ctgtcagcaa cattatagca ctccgacgtt cggtggaggc     300
accaagctgg aaatcaaacg ggct                                            324

<210> SEQ ID NO 10
<211> LENGTH: 33
<212> TYPE: DNA
<213> ORGANISM: Artificial
<220> FEATURE:
<223> OTHER INFORMATION: Synthetic Nucleotide sequence of LCDR1 of mAb
      3327

<400> SEQUENCE: 10
aaggccagtc aggatgtgag ttctgctgta gtt                                   33
```

```
<210> SEQ ID NO 11
<211> LENGTH: 21
<212> TYPE: DNA
<213> ORGANISM: Artificial
<220> FEATURE:
<223> OTHER INFORMATION: Synthetic Nucleotide sequence of LCDR2 of mAb
      3327

<400> SEQUENCE: 11
tgggcatcca cccggcacac t                                              21

<210> SEQ ID NO 12
<211> LENGTH: 24
<212> TYPE: DNA
<213> ORGANISM: Artificial
<220> FEATURE:
<223> OTHER INFORMATION: Synthetic Nucleotide sequence of LCDR3 of mAb
      3327

<400> SEQUENCE: 12
cagcaacatt atagcactcc gacg                                           24

<210> SEQ ID NO 13
<211> LENGTH: 108
<212> TYPE: PRT
<213> ORGANISM: Artificial
<220> FEATURE:
<223> OTHER INFORMATION: Synthetic Amino acid sequence of VL domain of
      mAb 3327

<400> SEQUENCE: 13

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Ser Ala
            20                  25                  30

Val Val Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Ser Thr Pro Thr
                85                  90                  95

Phe Gly Gly Gly Thr Lys Leu Glu Ile Lys Arg Ala
            100                 105

<210> SEQ ID NO 14
<211> LENGTH: 11
<212> TYPE: PRT
<213> ORGANISM: Artificial
<220> FEATURE:
<223> OTHER INFORMATION: Synthetic Amino acid sequence of LCDR1 of mAb
      3327

<400> SEQUENCE: 14

Lys Ala Ser Gln Asp Val Ser Ser Ala Val Val
1               5                   10

<210> SEQ ID NO 15
<211> LENGTH: 7
<212> TYPE: PRT
<213> ORGANISM: Artificial
<220> FEATURE:
<223> OTHER INFORMATION: Synthetic Amino acid sequence of LCDR2 of mAb
      3327
```

```
<400> SEQUENCE: 15

Trp Ala Ser Thr Arg His Thr
1               5

<210> SEQ ID NO 16
<211> LENGTH: 8
<212> TYPE: PRT
<213> ORGANISM: Artificial
<220> FEATURE:
<223> OTHER INFORMATION: Synthetic mino acid sequence of LCDR3 of mAb
      3327

<400> SEQUENCE: 16

Gln Gln His Tyr Ser Thr Pro Thr
1               5

<210> SEQ ID NO 17
<211> LENGTH: 32
<212> TYPE: PRT
<213> ORGANISM: Artificial
<220> FEATURE:
<223> OTHER INFORMATION: Synthetic Amino acid sequence of peptide fused
      to MBP

<400> SEQUENCE: 17

Gly Gly Ser His His His His His Gly Gly Ser Gln Asp Glu Gly
1               5                   10                  15

Ala Ala Ile Gly Leu Ala Trp Ile Pro Tyr Phe Gly Pro Ala Ala Glu
                20                  25                  30

<210> SEQ ID NO 18
<211> LENGTH: 676
<212> TYPE: PRT
<213> ORGANISM: Ebola virus

<400> SEQUENCE: 18

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
                20                  25                  30

Ile Pro Leu Gly Val Ile His Asn Ser Thr Leu Gln Val Ser Asp Val
                35                  40                  45

Asp Lys Leu Val Cys Arg Asp Lys Leu Ser Ser Thr Asn Gln Leu Arg
        50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
                100                 105                 110

Ile Lys Lys Pro Asp Gly Ser Glu Cys Leu Pro Ala Ala Pro Asp Gly
                115                 120                 125

Ile Arg Gly Phe Pro Arg Cys Arg Tyr Val His Lys Val Ser Gly Thr
        130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
                180                 185                 190
```

```
Phe Phe Ser Ser His Pro Leu Arg Glu Pro Val Asn Ala Thr Glu Asp
            195                 200                 205

Pro Ser Ser Gly Tyr Tyr Ser Thr Thr Ile Arg Tyr Gln Ala Thr Gly
210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
            275                 280                 285

Ala Phe Trp Glu Thr Lys Lys Asn Leu Thr Arg Lys Ile Arg Ser Glu
        290                 295                 300

Glu Leu Ser Phe Thr Val Val Ser Asn Gly Ala Lys Asn Ile Ser Gly
305                 310                 315                 320

Gln Ser Pro Ala Arg Thr Ser Ser Asp Pro Gly Thr Asn Thr Thr Thr
                325                 330                 335

Glu Asp His Lys Ile Met Ala Ser Glu Asn Ser Ser Ala Met Val Gln
            340                 345                 350

Val His Ser Gln Gly Arg Glu Ala Ala Val Ser His Leu Thr Thr Leu
        355                 360                 365

Ala Thr Ile Ser Thr Ser Pro Gln Ser Leu Thr Thr Lys Pro Gly Pro
        370                 375                 380

Asp Asn Ser Thr His Asn Thr Pro Val Tyr Lys Leu Asp Ile Ser Glu
385                 390                 395                 400

Ala Thr Gln Val Glu Gln His His Arg Arg Thr Asp Asn Asp Ser Thr
                405                 410                 415

Ala Ser Asp Thr Pro Ser Ala Thr Thr Ala Ala Gly Pro Pro Lys Ala
            420                 425                 430

Glu Asn Thr Asn Thr Ser Lys Ser Thr Asp Phe Leu Asp Pro Ala Thr
            435                 440                 445

Thr Thr Ser Pro Gln Asn His Ser Glu Thr Ala Gly Asn Asn Asn Thr
        450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
                485                 490                 495

Arg Arg Thr Arg Arg Glu Ala Ile Val Asn Ala Gln Pro Lys Cys Asn
            500                 505                 510

Pro Asn Leu His Tyr Trp Thr Thr Gln Asp Glu Gly Ala Ala Ile Gly
            515                 520                 525

Leu Ala Trp Ile Pro Tyr Phe Gly Pro Ala Ala Glu Gly Ile Tyr Ile
        530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605
```

-continued

```
Cys Ile Glu Pro His Asp Trp Thr Lys Asn Ile Thr Asp Lys Ile Asp
    610             615             620

Gln Ile Ile His Asp Phe Val Asp Lys Thr Leu Pro Asp Gln Gly Asp
625             630             635             640

Asn Asp Asn Trp Trp Thr Gly Trp Arg Gln Trp Ile Pro Ala Gly Ile
                645             650             655

Gly Val Thr Gly Val Ile Ile Ala Val Ile Ala Leu Phe Cys Ile Cys
            660             665             670

Lys Phe Val Phe
        675
```